United States Patent
Rabuka et al.

(10) Patent No.: US 9,181,343 B2
(45) Date of Patent: Nov. 10, 2015

(54) ANTIBODY SPECIFIC FOR CD22 AND METHODS OF USE THEREOF

(71) Applicant: Redwood Bioscience, Inc., Emeryville, CA (US)

(72) Inventors: David Rabuka, Kensington, CA (US); Robert George Edward Holgate, Royston (GB); Francis Joseph Carr, Aberdeen (GB)

(73) Assignee: Redwood Bioscience Inc., Emeryville, CA (US)

( * ) Notice: Subject to any disclaimer, the term of this patent is extended or adjusted under 35 U.S.C. 154(b) by 294 days.

(21) Appl. No.: 13/942,140

(22) Filed: Jul. 15, 2013

(65) Prior Publication Data

US 2014/0161870 A1     Jun. 12, 2014

Related U.S. Application Data

(60) Provisional application No. 61/673,630, filed on Jul. 19, 2012.

(51) Int. Cl.

| | |
|---|---|
| C07K 16/00 | (2006.01) |
| C12P 21/08 | (2006.01) |
| C12N 5/00 | (2006.01) |
| A61K 39/395 | (2006.01) |
| A61K 39/40 | (2006.01) |
| C07K 16/28 | (2006.01) |
| A61K 47/48 | (2006.01) |
| C07K 1/00 | (2006.01) |

(52) U.S. Cl.
CPC ....... *C07K 16/2851* (2013.01); *A61K 47/48561* (2013.01); *C07K 16/2803* (2013.01); *C07K 2317/24* (2013.01); *C07K 2317/76* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,484,892 A | 1/1996 | Tedder et al. | |
| 5,686,072 A | 11/1997 | Uhr et al. | |
| 5,789,554 A | 8/1998 | Leung et al. | |
| 5,980,895 A | 11/1999 | Pastan et al. | |
| 6,183,744 B1 | 2/2001 | Goldenberg | |
| 6,187,287 B1 | 2/2001 | Leung et al. | |
| 6,254,868 B1 | 7/2001 | Leung et al. | |
| 6,395,276 B1 | 5/2002 | Rybak et al. | |
| 6,653,104 B2 | 11/2003 | Goldenberg | |
| 7,037,498 B2 | 5/2006 | Cohen et al. | |
| 7,255,012 B2 | 8/2007 | Hedtke | |
| 7,321,026 B2 | 1/2008 | Leung | |
| 7,338,659 B2 | 3/2008 | Leung | |
| 7,355,011 B2 | 4/2008 | Popplewell et al. | |
| 7,355,012 B2 | 4/2008 | Pastan et al. | |
| 7,456,260 B2 | 11/2008 | Rybak et al. | |
| 7,521,541 B2 | 4/2009 | Eigenbrot et al. | |
| 7,534,427 B2 | 5/2009 | Goldenberg et al. | |
| 7,541,034 B1 | 6/2009 | Fitzgerald et al. | |
| 7,777,019 B2 | 8/2010 | Pastan et al. | |
| 7,829,086 B2 | 11/2010 | Hilbert et al. | |
| 7,855,275 B2 | 12/2010 | Eigenbrot et al. | |
| 8,226,945 B2 | 7/2012 | Ebens, Jr. et al. | |
| 2008/0118505 A1 | 5/2008 | Tedder | |
| 2009/0305411 A1 | 12/2009 | Fitzgerald et al. | |

FOREIGN PATENT DOCUMENTS

| | | |
|---|---|---|
| WO | 9859244 | 12/1998 |
| WO | 0074718 | 12/2000 |
| WO | 03072736 | 9/2003 |
| WO | 03105782 | 12/2003 |
| WO | 2007103470 | 9/2007 |
| WO | 2008070569 | 6/2008 |

OTHER PUBLICATIONS

Kreitman et al. (2011) "Antibody-Fusion Proteins: Anti-CD22 Recombinant Immunotoxin Moxetumomab Pasudotox" Clin Cancer Res 17(20):6398-6405.
Campana et al. (1985) "Human B cell development. I. Phenotypic differences of B lymphocytes in the bone marrow and peripheral lymphoid tissue" J Immunol 134(3):1524-1530.
Mansfield et al. (1997) "Recombinant RFB4 immunotoxins exhibit potent cytotoxic activity for CD22-bearing cells and tumors" Blood 90(5):2020-2026.
Amlot et al. (1993) "A phase I study of an anti-CD22-deglycosylated ricin A chain immunotoxin in the treatment of B-cell lymphomas resistant to conventional therapy" Blood 82(9):2624-2633.
GenBank Accession No. BAC01670 "immunoglobulin kappa light chain VLJ region [*Homo sapiens*]" dated Jul. 2, 2002.
GenBank Accession No. CAA75032 "immunoglobulin lambda heavy chain [*Homo sapiens*]" dated Aug. 19, 1998.
Ghetie et al. (1991) "Antitumor activity of Fab' and IgG-anti-CD22 immunotoxins in disseminated human B lymphoma grown in mice with severe combined immunodeficiency disease: effect on tumor cells in extranodal sites" Cancer Res 51(21):5876-5880.
Stimmel et al. (2000) "Site-specific conjugation on serine right-arrow cysteine variant monoclonal antibodies" J Biol Chem 275(39):30445-30450.
Vitetta et al. (1991) "Phase I immunotoxin trial in patients with B-cell lymphoma" 51(15):4052-4058.

*Primary Examiner* — Chun Dahle
(74) *Attorney, Agent, or Firm* — Carol L. Francis; Bozicevic, Field & Francis LLP

(57) ABSTRACT

The present disclosure provides antibodies specific for an epitope present on CD22. The antibodies are useful in various treatment, diagnostic, and monitoring applications, which are also provided.

30 Claims, 22 Drawing Sheets

|     | Kon      | Koff     | Kd       |
| --- | -------- | -------- | -------- |
| V12 | 4.93E+05 | 9.85E-05 | 2.00E-10 |
| V13 | 3.38E+05 | 1.32E-04 | 3.90E-10 |
| V14 | 3.92E+05 | 2.40E-04 | 6.14E-10 |
| V15 | 4.31E+05 | 2.15E-04 | 4.97E-10 |
| V16 | 3.68E+05 | 1.73E-04 | 4.71E-10 |
| V17 | 3.39E+05 | 2.52E-04 | 7.42E-10 |
| V18 | 3.26E+05 | 1.87E-04 | 5.72E-10 |
| V19 | 3.63E+05 | 2.01E-04 | 5.53E-10 |
| V20 | 4.01E+05 | 2.76E-04 | 6.89E-10 |

FIG. 5

Sequences of variable regions

Heavy chain variable regions

VH3
EVQLVESGGGLVKPGGSLKLSCAASGFAFSIYDMSWVRQAPGKGLEWVAYISSGGGTTYYPDTVKGRFTISRDNAKNTLYLQMSSLR
AEDTAMYYCARHSGYGSSYGVLFAYWGQGTLVTVSS (SEQ ID NO:3)

VH4
EVQLVESGGGLVKPGGSLRLSCAASGFAFSIYDMSWVRQAPGKGLEWVAYISSGGGTTYYPDTVKGRFTISRDNAKNSLYLQMSSLRA
EDTAMYYCARHSGYGSSYGVLFAYWGQGTLVTVSS (SEQ ID NO:4)

VH5
EVQLVESGGGLVKPGGSLKLSCAASGFAFSIYDMSWVRQAPGKGLEWVAYISSGGGTTYYPDTVKGRFTISRDNAKNSLYLQMNSLR
AEDTAMYYCARHSGYGSSYGVLFAYWGQGTLVTVSS (SEQ ID NO:5)

VH6
EVQLVESGGGLVKPGGSLKLSCAASGFAFSIYDMSWVRQAPGKGLEWVAYISSGGGTTYYPDTVKGRFTISRDNAKNSLYLQMSSLR
AEDTAMYYCARHSGYGSSYGVLFAYWGQGTLVTVSS (SEQ ID NO:6)

FIG. 7A

Sequences of variable regions light chain variable regions

VK1
DIQMTQSPSSLSASVGDRVTITCRASQDISNYLNWYQQKPGKAVKLLIYYTSILHSGVPSRFSGSGSGTDYTLTISSLQQEDFATYFCQQ
GNTLPWTFGGGTKVEIK (SEQ ID NO:7)

VK2
DIQMTQSPSSLSASVGDRVTITCRASQDISNYLNWYQQKPGKAVKLLIYYTSILHSGVPSRFSGSGSGTDYTLTISSLQPEDFATYFCQQG
NTLPWTFGGGTKVEIK (SEQ ID NO:8)

VK4
DIQMTQSPSSVSASVGDRVTITCRASQDISNYLNWYQQKPGKAPKLLIYYTSILHSGVPSRFSGSGSGTDYTLTISSLQPEDFATYFCQQG
NTLPWTFGGGTKVEIK (SEQ ID NO:9)

FIG. 7B

Variant 9 (VH3/VK1)
VH3
EVQLVESGGGLVKPGGSLKLSCAASGFAFSIYDMSWVRQAPGKGLEWVAYISSGGGTTYYPDTVKGRFTISRDNAKNTLYLQMSSLR
AEDTAMYYCARHSGYGSSYGVLFAYWGQGTLVTVSS (SEQ ID NO:3)
VK1
DIQMTQSPSSLSASVGDRVTITCRASQDISNYLNWYQQKPGKAVKLLIYYTSILHSGVPSRFSGSGSGTDYTLTISSLQQEDFATYFCQQ
GNTLPWTFGGGTKVEIK (SEQ ID NO:7)

Variant 10 (VH3/VK2)
VH3
EVQLVESGGGLVKPGGSLKLSCAASGFAFSIYDMSWVRQAPGKGLEWVAYISSGGGTTYYPDTVKGRFTISRDNAKNTLYLQMSSLR
AEDTAMYYCARHSGYGSSYGVLFAYWGQGTLVTVSS (SEQ ID NO:3)
VK2
DIQMTQSPSSLSASVGDRVTITCRASQDISNYLNWYQQKPGKAVKLLIYYTSILHSGVPSRFSGSGSGTDYTLTISSLQPEDFATYFCQQG
NTLPWTFGGGTKVEIK (SEQ ID NO:8)

Variant 11 (VH3/VK4)
VH3
EVQLVESGGGLVKPGGSLKLSCAASGFAFSIYDMSWVRQAPGKGLEWVAYISSGGGTTYYPDTVKGRFTISRDNAKNTLYLQMSSLR
AEDTAMYYCARHSGYGSSYGVLFAYWGQGTLVTVSS (SEQ ID NO:3)
VK4
DIQMTQSPSSVSASVGDRVTITCRASQDISNYLNWYQQKPGKAPKLLIYYTSILHSGVPSRFSGSGSGTDYTLTISSLQPEDFATYFCQQG
NTLPWTFGGGTKVEIK (SEQ ID NO:9)

FIG. 8A

Variant 12 (VH4/VK1)
VH4
EVQLVESGGGLVKPGGSLRLRLSCAASGFAFSIYDMSWVRQAPGKGLEWVAYISSGGGTTYYPDTVKGRFTISRDNAKNSLYLQMSSLRA
EDTAMYYCARHSGYGSSYGVLFAYWGQGTLVTVSS (SEQ ID NO:4)
VK1
DIQMTQSPSSLSASVGDRVTITCRASQDISNYLNWYQQKPGKAVKLLIYYTSILHSGVPSRFSGSGSGTDYTLTISSLQQEDFATYFCQQ
GNTLPWTFGGGTKVEIK (SEQ ID NO:7)

Variant 13 (VH4/VK2)
VH4
EVQLVESGGGLVKPGGSLRLRLSCAASGFAFSIYDMSWVRQAPGKGLEWVAYISSGGGTTYYPDTVKGRFTISRDNAKNSLYLQMSSLRA
EDTAMYYCARHSGYGSSYGVLFAYWGQGTLVTVSS (SEQ ID NO:4)
VK2
DIQMTQSPSSLSASVGDRVTITCRASQDISNYLNWYQQKPGKAVKLLIYYTSILHSGVPSRFSGSGSGTDYTLTISSLQPEDFATYFCQQG
NTLPWTFGGGTKVEIK (SEQ ID NO:8)

Variant 14 (VH4/VK4)
VH4
EVQLVESGGGLVKPGGSLRLRLSCAASGFAFSIYDMSWVRQAPGKGLEWVAYISSGGGTTYYPDTVKGRFTISRDNAKNSLYLQMSSLRA
EDTAMYYCARHSGYGSSYGVLFAYWGQGTLVTVSS (SEQ ID NO:4)
VK4
DIQMTQSPSSVSASVGDRVTITCRASQDISNYLNWYQQKPGKAPKLLIYYTSILHSGVPSRFSGSGSGTDYTLTISSLQPEDFATYFCQQG
NTLPWTFGGGTKVEIK (SEQ ID NO:9)

FIG. 8B

Variant 15 (VH5/VK1)
VH5
EVQLVESGGGLVKPGGSLKLSCAASGFAFSIYDMSWVRQAPGKGLEWVAYISSGGGTTYYPDTVKGRFTISRDNAKNSLYLQMNSLR
AEDTAMYYCARHSGYGSSYGVLFAYWGQGTLVTVSS (SEQ ID NO:5)
VK1
DIQMTQSPSSLSASVGDRVTITCRASQDISNYLNWYQQKPGKAVKLLIYYTSILHSGVPSRFSGSGSGTDYTLTISSLQQEDFATYFCQQ
GNTLPWTFGGGTKVEIK (SEQ ID NO:7)

Variant 16 (VH5/VK2)
VH5
EVQLVESGGGLVKPGGSLKLSCAASGFAFSIYDMSWVRQAPGKGLEWVAYISSGGGTTYYPDTVKGRFTISRDNAKNSLYLQMNSLR
AEDTAMYYCARHSGYGSSYGVLFAYWGQGTLVTVSS (SEQ ID NO:5)
VK2
DIQMTQSPSSLSASVGDRVTITCRASQDISNYLNWYQQKPGKAVKLLIYYTSILHSGVPSRFSGSGSGTDYTLTISSLQPEDFATYFCQQG
NTLPWTFGGGTKVEIK (SEQ ID NO:8)

Variant 17 (VH5/VK4)
VH5
EVQLVESGGGLVKPGGSLKLSCAASGFAFSIYDMSWVRQAPGKGLEWVAYISSGGGTTYYPDTVKGRFTISRDNAKNSLYLQMNSLR
AEDTAMYYCARHSGYGSSYGVLFAYWGQGTLVTVSS (SEQ ID NO:5)
VK4
DIQMTQSPSSVSASVGDRVTITCRASQDISNYLNWYQQKPGKAPKLLIYYTSILHSGVPSRFSGSGSGTDYTLTISSLQPEDFATYFCQQG
NTLPWTFGGGTKVEIK (SEQ ID NO:9)

FIG. 8C

Variant 18 (VH6/VK1)
VH6
EVQLVESGGGLVKPGGSLKLSCAASGFAFSIYDMSWVRQAPGKGLEWVAYISSGGGTTYYPDTVKGRFTISRDNAKNSLYLQMSSLR
AEDTAMYYCARHSGYGSSYGVLFAYWGQGTLVTVSS (SEQ ID NO:6)

VK1
DIQMTQSPSSLSASVGDRVTITCRASQDISNYLNWYQQKPGKAVKLLIYYTSILHSGVPSRFSGSGSGTDYTLTISSLQQEDFATYFCQQ
GNTLPWTFGGGTKVEIK (SEQ ID NO:7)

Variant 19 (VH6/VK2)
VH6
EVQLVESGGGLVKPGGSLKLSCAASGFAFSIYDMSWVRQAPGKGLEWVAYISSGGGTTYYPDTVKGRFTISRDNAKNSLYLQMSSLR
AEDTAMYYCARHSGYGSSYGVLFAYWGQGTLVTVSS (SEQ ID NO:6)

VK2
DIQMTQSPSSLSASVGDRVTITCRASQDISNYLNWYQQKPGKAVKLLIYYTSILHSGVPSRFSGSGSGTDYTLTISSLQPEDFATYFCQQG
NTLPWTFGGGTKVEIK (SEQ ID NO:8)

FIG. 8D

Variant 20 (VH6/VK4)
VH6
EVQLVESGGGLVKPGGSLKLSCAASGFAFSIYDMSWVRQAPGKGLEWVAYISSGGGTTYYPDTVKGRFTISRDNAKNSLYLQMSSLR
AEDTAMYYCARHSGYGSSYGVLFAYWGQGTLVTVSS (SEQ ID NO:6)

VK4
DIQMTQSPSSVSASVGDRVTITCRASQDISNYLNWYQQKPGKAPKLLIYYTSILHSGVPSRFSGSGSGTDYTLTISSLQPEDFATYFCQQG
NTLPWTFGGGTKVEIK (SEQ ID NO:9)

FIG. 8E

| | | |
|---|---|---|
| isoform2 | MHLLGPWLLLLVLEYLAFSDSSKWVFEHPETLYAWEGACVWIPCTYRALDGDLESFILFH | 60 |
| isoform4 | MHLLGPWLLLLVLEYLAFSDSSKWVFEHPETLYAWEGACVWIPCTYRALDGDLESFILFH | 60 |
| isoform1 | MHLLGPWLLLLVLEYLAFSDSSKWVFEHPETLYAWEGACVWIPCTYRALDGDLESFILFH | 60 |
| isoform3 | MHLLGPWLLLLVLEYLAFSDSSKWVFEHPETLYAWEGACVWIPCTYRALDGDLESFILFH | 60 |
| | ************************************************************ | |
| isoform2 | NPEYNKNTSKFDGTRLYESTKDGKVPSEQKRVQFLGDKNKNCTLSIHPVHLNDSGQLGLR | 120 |
| isoform4 | NPEYNKNTSKFDGTRLYESTKDGKVPSEQKRVQFLGDKNKNCTLSIHPVHLNDSGQLGLR | 120 |
| isoform1 | NPEYNKNTSKFDGTRLYESTKDGKVPSEQKRVQFLGDKNKNCTLSIHPVHLNDSGQLGLR | 120 |
| isoform3 | NPEYNKNTSKFDGTRLYESTKDGKVPSEQKRVQFLGDKNKNCTLSIHPVHLNDSGQLGLR | 120 |
| | ************************************************************ | |
| isoform2 | MESKTEKWMERIHLNVSERPFPPHIQLPPEIQESQEVTLTCLLNFSCYGYPIQLQWLLEG | 180 |
| isoform4 | MESKTEKWMERIHLNVSERPFPPHIQLPPEIQESQEVTLTCLLNFSCYGYPIQLQWLLEG | 180 |
| isoform1 | MESKTEKWMERIHLNVSERPFPPHIQLPPEIQESQEVTLTCLLNFSCYGYPIQLQWLLEG | 180 |
| isoform3 | MESKTEKWMERIHLNVSERPFPPHIQLPPEIQESQEVTLTCLLNFSCYGYPIQLQWLLEG | 180 |
| | ************************************************************ | |
| isoform2 | VPMRQAAVTSTSLTIKSVFTRSELKFSPQWSHHGKIVTCQLQDADGKFLSNDTVQLNVKH | 240 |
| isoform4 | VPMRQAAVTSTSLTIKSVFTRSELKFSPQWSHHGKIVTCQLQDADGKFLSNDTVQLNVKH | 240 |
| isoform1 | VPMRQAAVTSTSLTIKSVFTRSELKFSPQWSHHGKIVTCQLQDADGKFLSNDTVQLNVKH | 240 |
| isoform3 | VPMRQAAVTSTSLTIKSVFTRSELKFSPQWSHHGKIVTCQLQDADGKFLSNDTVQLNVKH | 240 |
| | ************************************************************ | |
| isoform2 | TPKLEIKVTPSDAIVREGDSVTMTCEVSSSNPEYTTVSWLKDGTSLKKQNTFTLNLREVT | 300 |
| isoform4 | ------------------------------------------------------------ | |
| isoform1 | TPKLEIKVTPSDAIVREGDSVTMTCEVSSSNPEYTTVSWLKDGTSLKKQNTFTLNLREVT | 300 |
| isoform3 | TPKLEIKVTPSDAIVREGDSVTMTCEVSSSNPEYTTVSWLKDGTSLKKQNTFTLNLREVT | 300 |

FIG. 9A

```
isoform2  KDQSGKYCCQVSNDVGPGRSEEVFLQVQ------------------------------    328
isoform4  ------------------------------------------------------------      -
isoform1  KDQSGKYCCQVSNDVGPGRSEEVFLQVQYAPEPSTVQILHSPAVEGSQVEFLCMSLANPL    360
isoform3  KDQSGKYCCQVSNDVGPGRSEEVFLQVQYAPEPSTVQILHSPAVEGSQVEFLCMSLANPL    360 isoform2  ----------------------------------------------------YPPK        332
isoform4  ------------------------------------------------------PPK        243
isoform1  PTNYTWYHNGKEMQGRTEEKVHIPKILPWHAGTYSCVAENILGTGQRGPGAELDVQYPPK    420
isoform3  PTNYTWYHNGKEMQGRTEEKVHIPKILPWHAGTYSCVAENILGTGQRGPGAELDVQYPPK    420
                                                              *** isoform2  KVTTVIQNPMPIREGDTVTLSCNYNSSNPSVTRYEWKPHGAWEEPSLGVLKIQNVGWDNT    392
isoform4  KVTTVIQNPMPIREGDTVTLSCNYNSSNPSVTRYEWKPHGAWEEPSLGVLKIQNVGWDNT    303
isoform1  KVTTVIQNPMPIREGDTVTLSCNYNSSNPSVTRYEWKPHGAWEEPSLGVLKIQNVGWDNT    480
isoform3  KVTTVIQNPMPIREGDTVTLSCNYNSSNPSVTRYEWKPHGAWEEPSLGVLKIQNVGWDNT    480
          ************************************************************ isoform2  TIACAACNSWCSWASPVALNVQYAPRDVRVRKIKPLSEIHSGNSVSLQCDFSSSHPKEVQ    452
isoform4  TIACAACNSWCSWASPVALNVQYAPRDVRVRKIKPLSEIHSGNSVSLQCDFSSSHPKEVQ    363
isoform1  TIACAACNSWCSWASPVALNVQYAPRDVRVRKIKPLSEIHSGNSVSLQCDFSSSHPKEVQ    540
isoform3  TIACAACNSWCSWASPVALNVQYAPRDVRVRKIKPLSEIHSGNSVSLQCDFSSSHPKEVQ    540
          ************************************************************ isoform2  FFWEKNGRLLGKESQLNFDSISPEDAGSYSCWVNNSIGQTASKAWTLEVLYAPRRLRVSM    512
isoform4  FFWEKNGRLLGKESQLNFDSISPEDAGSYSCWVNNSIGQTASKAWTLEVLYAPRRLRVSM    423
isoform1  FFWEKNGRLLGKESQLNFDSISPEDAGSYSCWVNNSIGQTASKAWTLEVLYAPRRLRVSM    600
isoform3  FFWEKNGRLLGKESQLNFDSISPEDAGSYSCWVNNSIGQTASKAWTLEVLYAPRRLRVSM    600
          ************************************************************ isoform2  SPGDQVMEGKSATLTCESDANPPVSHYTWFDWNNQSLPYHSQKLRLEPVKVQHSGAYWCQ    572
isoform4  SPGDQVMEGKSATLTCESDANPPVSHYTWFDWNNQSLPYHSQKLRLEPVKVQHSGAYWCQ    483
isoform1  SPGDQVMEGKSATLTCESDANPPVSHYTWFDWNNQSLPYHSQKLRLEPVKVQHSGAYWCQ    660
isoform3  SPGDQVMEGKSATLTCESDANPPVSHYTWFDWNNQSLPYHSQKLRLEPVKVQHSGAYWCQ    660
          ************************************************************
```

FIG. 9B

```
isoform2  GTNSVGKGRSPLSTLTVYYSPETIGRRVAVGLGSCLAILILAICGLKLQRRWKRTQSQQG  632
isoform4  GTNSVGKGRSPLSTLTVYYSPETIGRRVAVGLGSCLAILILAICGLKLQRRWKRTQSQQG  543
isoform1  GTNSVGKGRSPLSTLTVYYSPETIGRRVAVGLGSCLAILILAICGLKLQRRWKRTQSQQG  720
isoform3  GTNSVGKGRSPLSTLTVYYSPETIGRRVAVGLGSCLAILILAICGLKLQRRWKRTQSQQG  720
          ************************************************************ isoform2  LQENSSGQSFFVRNKKVRRAPLSEGPHSLGCYNPMMEDGISYTTLRFPEMNIPRTGDAES  692
isoform4  LQENSSGQSFFVRNKKVRRAPLSEGPHSLGCYNPMMEDGISYTTLRFPEMNIPRTGDAES  603
isoform1  LQENSSGQSFFVRNKKVRRAPLSEGPHSLGCYNPMMEDGISYTTLRFPEMNIPRTGDAES  780
isoform3  LQENSSGQSFFVRNKKKRCRVLR--------------------------------DAET  746
          ***************  *                                      ***:

isoform2  SEMQRPPPDCDDTVTYSALHKRQVGDYENVIPDFPEDEGIHYSELIQFGVGERPQAQENV  752
isoform4  SEMQRPPPDCDDTVTYSALHKRQVGDYENVIPDFPEDEGIHYSELIQFGVGERPQAQENV  663
isoform1  SEMQRPPPDCDDTVTYSALHKRQVGDYENVIPDFPEDEGIHYSELIQFGVGERPQAQENV  840
isoform3  SPGLR-------------------------------------------------------  751
          * isoform2  DYVILKH  759
isoform4  DYVILKH  670
isoform1  DYVILK-  846
isoform3  -------
```

FIG. 9C

ANTIBODY SPECIFIC FOR CD22 AND METHODS OF USE THEREOF

CROSS-REFERENCE TO RELATED APPLICATIONS

This application claims priority benefit of U.S. provisional application Ser. No. 61/673,630, filed Jul. 19, 2012, which application is incorporated herein by reference in its entirety.

INTRODUCTION

CD22, a lineage-restricted B cell antigen that belongs to the Ig superfamily, is expressed on the surface of many types of malignant B cells, as well as on normal mature B lymphocytes.

SUMMARY OF THE INVENTION

The present disclosure provides antibodies specific for CD22. The antibodies are useful in various treatment, diagnostic, and monitoring applications, which are also provided.

BRIEF DESCRIPTION OF THE DRAWINGS

FIG. 5 depicts binding affinities of variant antibodies to human CD22.

FIGS. 7A and 7B provide an amino acid sequences of anti-CD22 heavy chain (FIG. 7A) and light chain (FIG. 7B) variable regions.

FIGS. 8A-E provide amino acid sequences of anti-CD22 antibody variant antibodies 9-20.

FIGS. 9A-C provide amino acid sequences of CD22 isoforms (Top to bottom: SEQ ID NOs:35-38).

DEFINITIONS

Figure 1A:
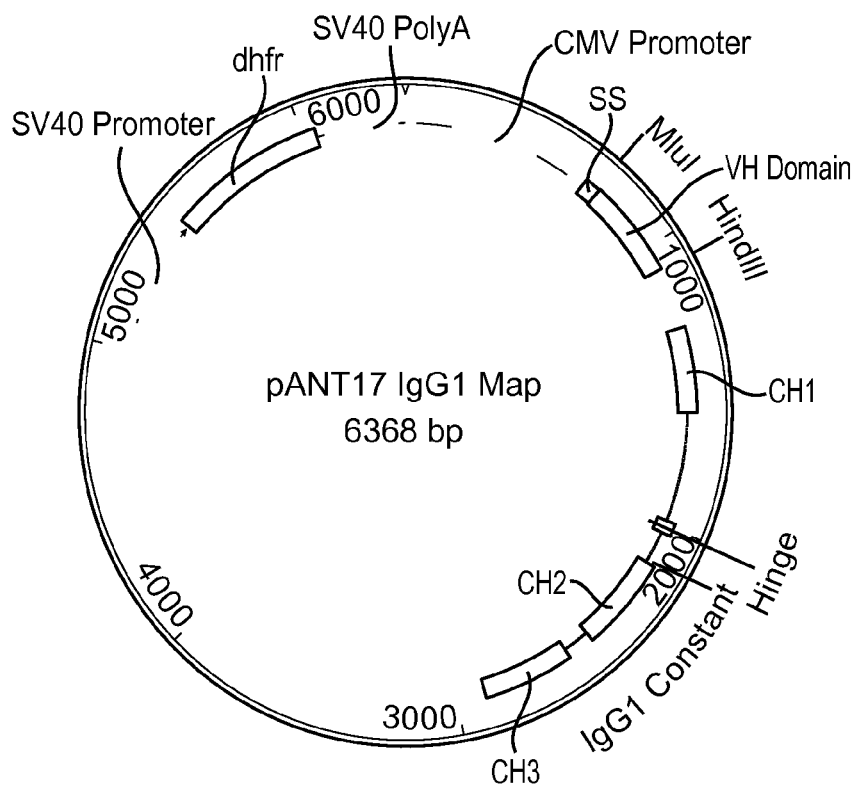
FIGS. 1A and 1B depict constructs encoding heavy (FIG. 1A) and light (FIG. 1B) chains of chimeric or humanized anti-CD22 antibodies.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A subject anti-CD22 binds specifically to an epitope within a CD-22 polypeptide. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a subject anti-CD22 Ab that, when administered to a mammal or other subject for treating a disease, is sufficient to effect such treatment for the disease. The "therapeutically effective amount" will vary depending on the anti-CD22 Ab, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. In some cases, a biological sample will include B cells.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antibody" includes a plurality of such antibodies and reference to "the CDR" includes reference to one or more CDRs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides antibodies specific for CD22. The antibodies are useful in various treatment, diagnostic, and monitoring applications, which are also provided.

Antibodies

A subject antibody specifically binds a CD22 polypeptide, where the epitope comprises amino acid residues within a CD22 antigen (e.g., within amino acids 1 to 847, within amino acids 1-759, within amino acids 1-751, or within amino acids 1-670, of a CD22 amino acid sequence depicted in FIGS. 9A-C).

The CD22 epitope can be formed by a polypeptide having at least about 75%, at least about 80%, at least about 85%, at least about 90%, at least about 95%, at least about 98%, at least about 99%, or 100%, amino acid sequence identity to a contiguous stretch of from about 500 amino acids to about 670 amino acids of the human CD22 isoform 4 amino acid sequence depicted in FIGS. 9A-C. The CD22 epitope can be formed by a polypeptide having at least about 75%, at least about 80%, at least about 85%, at least about 90%, at least about 95%, at least about 98%, at least about 99%, or 100%, amino acid sequence identity to a contiguous stretch of from about 500 amino acids to about 751 amino acids of the human CD22 isoform 3 amino acid sequence depicted in FIGS. 9A-C. The CD22 epitope can be formed by a polypeptide having at least about 75%, at least about 80%, at least about 85%, at least about 90%, at least about 95%, at least about 98%, at least about 99%, or 100%, amino acid sequence identity to a contiguous stretch of from about 500 amino acids to about 759 amino acids of the human CD22 isoform 2 amino acid sequence depicted in FIGS. 9A-C. The CD22 epitope can be formed by a polypeptide having at least about 75%, at least about 80%, at least about 85%, at least about 90%, at least about 95%, at least about 98%, at least about 99%, or 100%, amino acid sequence identity to a contiguous stretch of from about 500 amino acids to about 847 amino acids of the human CD22 isoform 1 amino acid sequence depicted in FIGS. 9A-C.

A subject antibody exhibits high affinity binding to CD22. For example, a subject antibody binds to CD22 with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject antibody binds to an epitope present on CD22 with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

An anti-CD22 antibody of the present disclosure can in some cases induce apoptosis in a cell that expresses CD22 on its cell surface.

A "CD22 antigen" or "CD22 polypeptide" can comprises an amino acid sequence having at least about 75%, at least about 80%, at least about 90%, at least about 95%, at least about 98%, at least about 99%, or 100%, amino acid sequence identity to a contiguous stretch of from about 500 amino acids (aa) to about 847 aa (isoform 1), to about 759 aa (isoform 2), to about 751 aa (isoform 3), or to about 670 aa (isoform 4) of a CD22 isoform 1, 2, 3, or 4 amino acid sequence depicted in FIGS. 9A-C.

The term "antibody" refers to a protein comprising one or more (e.g., one or two) heavy chain variable regions (VH) and/or one or more (e.g., one or two) light chain variable regions (VL), or subfragments thereof capable of binding an epitope. The VH and VL regions can be further subdivided into regions of hypervariability, termed "complementarity determining regions (CDR)", interspersed with regions that are more conserved, termed "framework regions (FR)". The extent of the FR and CDRs has been precisely defined (see, Kabat, et al. (1991) Sequences of Proteins of Immunological Interest, Fifth Edition, U.S. Department of Health and Human Services, NIH Publication No. 91-3242; Chothia et al. (1987) J. Mol. Biol. 196: 901-917). A VH can comprise three CDRs and four FRs arranged from N-terminus to C-terminus in the following order: FR1, CDR1, FR2, CDR2, FR3, CDR3, FR4. Similarly, a VL can comprise three CDRs and four FRs arranged from N-terminus to C-terminus in the following order: FR1, CDR1, FR2, CDR2, FR3, CDR3, FR4.

The VH or VL chain of an antibody can further include all or part of a heavy or light chain constant region, to thereby form a heavy or light immunoglobulin chain, respectively. In one embodiment, the antibody is a tetramer of two heavy and two light chains, wherein the heavy and light chains are interconnected by, for example, disulphide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes intact immunoglobulins of types IgA, IgG, IgE, IgD, IgM and subtypes thereof. In some embodiments, a subject antibody is an IgG isotype. In some embodiments, a subject antibody is an IgG1 isotype.

As used herein the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

In some embodiments, a subject antibody does not comprise a full-length immunoglobulin heavy chain and a full-length immunoglobulin light chain, and instead comprises antigen-binding fragments of a full-length immunoglobulin heavy chain and a full-length immunoglobulin light chain. In some embodiments, the antigen-binding fragments are contained on separate polypeptide chains; in other embodiments, the antigen-binding fragments are contained within a single polypeptide chain. The term "antigen-binding fragment" refers to one or more fragments of a full-length antibody that are capable of specifically binding to CD22, as described above. Examples of binding fragments include (i) a Fab fragment (a monovalent fragment consisting of the VL, VH, CL and CH1 domains; (ii) a F(ab')$_2$ fragment (a bivalent fragment comprising two Fab fragments linked by a disulfide bridge at the hinge region; (iii) a Fd fragment (consisting of the VH and CH1 domains); (iv) a Fv fragment (consisting of the VH and VL domains of a single arm of an antibody); (v) a dAb fragment (consisting of the VH domain); (vi) an isolated CDR; (vii) a single chain Fv (scFv) (consisting of the VH and VL domains of a single arm of an antibody joined by a synthetic linker using recombinant means such that the VH and VL domains pair to form a monovalent molecule); (viii) diabodies (consisting of two scFvs in which the VH and VL domains are joined such that they do not pair to form a monovalent molecule; the VH of each one of the scFv pairs with the VL domain of the other scFv to form a bivalent molecule); (ix) bi-specific antibodies (consisting of at least two antigen binding regions, each region binding a different epitope). In some embodiments, a subject antibody fragment is a Fab fragment. In some embodiments, a subject antibody fragment is a single-chain antibody (scFv).

In some embodiments, a subject antibody is a recombinant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

In some embodiments, a subject antibody comprises: a) a heavy chain comprising a VH region having the amino acid sequence EVQLVESGGGLVKPGGSLX$^1$LSCAASGFA FSIYDMSWVRQAPGKGLEWVAYISSGGGTTYYPDT VKGRFTISRDNAKNX$^2$LYLQMX$^3$SLRAEDTAMYYCA RHSGYGSSYGVLFAYWGQGTLVTVSS (SEQ ID NO:1), where X$^1$ is K (Lys) or R (Arg); X$^2$ is S (Ser) or T (Thr); and X$^3$ is N (Asn) or S (Ser); and b) an immunoglobulin light chain.

A light chain can have any suitable V$_L$ amino acid sequence, so long as the resulting antibody binds specifically to CD22.

Exemplary V$_L$ amino acid sequences include:
DIQMTQSPSSLSASVGDRVTIT-CRASQDISNYLNWYQQKPGKAVKLLIYY TSILHS-GVPSRFSGSGSGTDYTLTISSLQQEDFA-TYFCQQGNTLPWTFGGGTKVEIK (SEQ ID NO:7; VK1);

DIQMTQSPSSLSASVGDRVTIT-CRASQDISNYLNWYQQKPGKAVKLLIYY TSILHS-GVPSRFSGSGSGTDYTLTISSLQPEDFA-TYFCQQGNTLPWTFGGGTKVEIK (SEQ ID NO:8; VK2); and DIQMTQSPSSVSASVGDRVTIT-CRASQDISNYLNWYQQKPGKAPKLLIYY TSILHS-GVPSRFSGSGSGTDYTLTISSLQPEDFA-TYFCQQGNTLPWTFGGGTKVEIK (SEQ ID NO:9; VK4).

Thus, e.g., a subject anti-CD22 antibody can comprise: a) a heavy chain comprising a VH region having the amino acid sequence set forth in SEQ ID NO:1); and a light chain comprising the VL region of VK1. In other cases, a subject anti-CD22 antibody can comprise: a) a heavy chain comprising a VH region having the amino acid sequence set forth in SEQ ID NO:1); and a light chain comprising the VL region of VK2. In still other cases, a subject anti-CD22 antibody can comprise: a) a heavy chain comprising a VH region having the amino acid sequence set forth in SEQ ID NO:1); and a light chain comprising the VL region of VK4.

In some instances, a subject anti-CD22 antibody comprises: a) an immunoglobulin light chain comprising the amino acid sequence DIQMTQSPSSX$^1$SASVGDR VTITCRASQDISNYLNWYQQKPGKAX$^2$KLLIYYTSIL HSGVPSRFSGSGSGTDYTLTISSLQX$^3$EDFATYFCQQG NTLPWTFGGGTKVEIK (SEQ ID NO:2), where X$^1$ is L (Leu) or V (Val); X$^2$ is V (Val) or P (Pro); and X$^3$ is Q (Gln) or P (Pro); and b) an immunoglobulin heavy chain. The heavy chain can comprise an amino acid sequence selected from:
EVQLVESGGGLVKPGGSLKLSCAASG-FAFSIYDMSWVRQAPGKGLEWVA YISSGGGTTYYP-DTVKGRFTISRDNAKNTLYLQMSSL-RAEDTAMYYCARHSGYGSSYG VLFAYWGQGTLVTVSS (SEQ ID NO:3; VH3);
EVQLVESGGGLVKPGGSLRLSCAASG-FAFSIYDMSWVRQAPGKGLEWVA YISSGGGTTYYP-DTVKGRFTISRDNAKNSLYLQMSSL-RAEDTAMYYCARHSGYGSSYGV LFAYWGQGTLVTVSS (SEQ ID NO:4; VH4);
EVQLVESGGGLVKPGGSLKLSCAASG-FAFSIYDMSWVRQAPGKGLEWVA YISSGGGTTYYP- DTVKGRFTISRDNAKNSLYLQMNSL-
RAEDTAMYYCARHSGYGSSYG
VLFAYWGQGTLVTVSS (SEQ ID NO:5; VH5); and
EVQLVESGGGLVKPGGSLKLSCAASG-
FAFSIYDMSWVRQAPGKGLEWVA YISSGGGTTYYP-
DTVKGRFTISRDNAKNSLYLQMSSL-
RAEDTAMYYCARHSGYGSSYGV
LFAYWGQGTLVTVSS (SEQ ID NO:6; VH6).

Linkers suitable for use a subject antibody include "flexible linkers." If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

A subject antibody can be "humanized." The term "humanized antibody" refers to an antibody comprising at least one chain comprising variable region framework residues substantially from a human antibody chain (referred to as the acceptor immunoglobulin or antibody) and at least one CDR substantially from a mouse antibody, (referred to as the donor immunoglobulin or antibody). See, Queen et al., Proc. Natl. Acad. Sci. USA 86:10029 10033 (1989), U.S. Pat. Nos. 5,530,101, 5,585,089, 5,693,761, WO 90/07861, and U.S. Pat. No. 5,225,539. The constant region(s), if present, can also be substantially or entirely from a human immunoglobulin. Methods of making humanized antibodies are known in the art. See, e.g., U.S. Pat. No. 7,256,273.

The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

In some embodiments, a subject antibody comprises scFv multimers. For example, in some embodiments, a subject antibody is an scFv dimer (e.g., comprises two tandem scFv ($scFv_2$)), an scFv trimer (e.g., comprises three tandem scFv ($scFv_3$)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 10 amino acids in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFV multimer is humanized, as described above.

In some embodiments, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to a subject antibody that comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

The present disclosure also provides anti-CD22 antibodies having an attached moiety of interest, e.g. a detectable label, drug, half-life-extending moiety, and the like. Modification of antibodies can be accomplished by a variety of synthetic and/or recombinant methods. The moiety or moieties attached to an antibody can provide for one or more of a wide variety of functions or features. Exemplary moieties include detectable labels (e.g., dye labels (e.g., chromophores, fluorophores), biophysical probes (spin labels, nuclear magnetic resonance (NMR) probes), Förster Resonance Energy Transfer (FRET)-type labels (e.g., at least one member of a FRET pair, including at least one member of a fluorophore/quencher pair), Bioluminescence Resonance Energy Transfer (BRET)-type labels (e.g., at least one member of a BRET pair), immunodetectable tags (e.g., FLAG, His(6), and the like); water soluble polymers (e.g., PEGylation); purification tags (e.g., to facilitate isolation by affinity chromatography (e.g., attachment of a FLAG epitope; membrane localization domains (e.g., lipids or glycophosphatidylinositol (GPI)-type anchors); immobilization tags (e.g., to facilitate attachment of the polypeptide to a surface, including selective attachment); drugs (e.g., to facilitate drug targeting, e.g., through attachment of the drug to an antibody); and the like.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject antibody comprises a poly (ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a PEG polymer. In some embodiments, a subject scFv multimer is covalently linked to a PEG polymer. Methods and reagents suitable for PEGylation of a protein are well known in the art and may be found in, e.g., U.S. Pat. No. 5,849,860. PEG suitable for conjugation to a protein is generally soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons.

The PEG conjugated to the subject antibody can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., a subject antibody can comprise a covalently linked carbohydrate or polysaccharide moiety. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. Glycosylation can be accomplished by, for example, recombination production in a host cell having the desired glycosylation machinery.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2, 4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody can in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3H$, $^{125}I$, $^{35}S$, $^{14}C$, or $^{32}P$), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use as a detectable label, e.g., in imaging, e.g., imaging procedures carried out on humans. Non-limiting examples of labels include radioisotope such as $^{123}I$ (iodine), $^{18}F$ (fluorine), $^{99}Tc$ (technetium), $^{111}In$ (indium), and $^{67}Ga$ (gallium), and contrast agent such as gadolinium (Gd), dysprosium, and iron. Radioactive Gd isotopes ($^{153}Gd$) also are available and suitable for imaging procedures in non-human mammals.

A subject antibody can be labeled using standard techniques. For example, a subject antibody can be iodinated using chloramine T or 1,3,4,6-tetrachloro-3α,6α-dephenylglycouril. For fluorination, fluorine is added to a subject antibody during the synthesis by a fluoride ion displacement reaction. See, Muller-Gartner, H., TIB Tech., 16:122-130

(1998) and Saji, H., Crit. Rev. Ther. Drug Carrier Syst., 16(2): 209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, the like; provide for secretion of the fusion protein from a cell; provide an epitope tag, e.g., (His)n, e.g., 6His, and the like; provide for secretion of the fusion protein from a cell; provide an epitope tag, e.g., GST, hemagglutinin (HA; e.g., CYPYDVPDYA; SEQ ID NO:10), FLAG (e.g., DYKDDDDK; SEQ ID NO:11), c-myc (e.g., CEQKLISEEDL; SEQ ID NO:12), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Examples of affinity domains include His5 (HHHHH) (SEQ ID NO:13), His X6 (HHHHHH) (SEQ ID NO:14), C-myc (EQKLISEEDL) (SEQ ID NO:15), Flag (DYKDDDDK) (SEQ ID NO:16), StrepTag (WSHPQFEK) (SEQ ID NO:17), hemagglutinin, e.g., HA Tag (YPYDVPDYA; SEQ ID NO:18), glutathinone-S-transferase (GST), thioredoxin, cellulose binding domain, RYIRS (SEQ ID NO:19), Phe-His-His-Thr (SEQ ID NO:20), chitin binding domain, S-peptide, T7 peptide, SH2 domain, C-end RNA tag, WEAAAREAC-CRECCARA (SEQ ID NO:21), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

In some embodiments, a subject antibody comprises a polyamine modification. A subject antibody can be modified with polyamines that are either naturally occurring or synthetic. See, for example, U.S. Pat. No. 5,670,477. Useful naturally occurring polyamines include putrescine, spermidine, spermine, 1,3-deaminopropane, norspermidine, synhomospermidine, thermine, thermospermine, caldopentamine, homocaldopentamine, and canavalmine. Putrescine, spermidine and spermine are particularly useful. Synthetic polyamines are composed of the empirical formula $C_xH_yN_z$, can be cyclic or acyclic, branched or unbranched, hydrocarbon chains of 3-12 carbon atoms that further include 1-6 NR or $N(R)_2$ moieties, wherein R is H, $(C_1-C_4)$ alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated into a liposome.

Where an anti-CD22 antibody of the present disclosure comprises a covalently linked heterologous moiety, the heterologous moiety can be linked to the anti-CD22 heavy and/or light chain directly or via a linker. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Examples of flexible linkers include glycine polymers (G)n, glycine-serine polymers (including, for example, (GS)n, GSGGSn (SEQ ID NO:22) and GGGSn (SEQ ID NO:23), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11 173-142 (1992)). Exemplary flexible linkers include, but are not limited GGSG (SEQ ID NO:24), GGSGG (SEQ ID NO:25), GSGSG (SEQ ID NO: 26), GSGGG (SEQ ID NO: 27), GGGSG (SEQ ID NO: 28), GSSSG (SEQ ID NO: 29), and the like. The ordinarily skilled artisan will recognize that design of a peptide conjugated to any elements described above can include linkers that are all or partially flexible, such that the linker can include a flexible linker as well as one or more portions that confer less flexible structure.

Methods for Modification of Antibodies

The antibodies can be modified to have a covalently attached heterologous moiety (e.g., detectable label, drug, etc.) by use of any of a variety of methods. The present disclosure provides an anti-CD22 antibody conjugated to a moiety of interest, where an anti-CD22 antibody conjugated to a moiety of interest is referred to as an "anti-CD22 antibody conjugate." An anti-CD22 antibody conjugate of the present disclosure can include: 1) Ig heavy chain constant region conjugated to a moiety of interest; and an Ig light chain constant region conjugated to a moiety of interest; 2) an Ig heavy chain constant region conjugated to a moiety of interest; and an Ig light chain constant region that is not conjugated to a moiety of interest; or 3) an Ig heavy chain constant region that is not conjugated to a moiety of interest; and an Ig light chain constant region conjugated to a moiety of interest. A subject anti-CD22 antibody conjugate can also include VH and/or VL domains.

In one example, the antibody can be modified to include a 2-formylglycine residue, which can serve as a chemical handle for attachment of a heterologous moiety. For example, the heavy and/or light chain constant region of an anti-CD22 of the present disclosure can be modified to include an amino acid sequence of a sulfatase motif which is capable of being converted by action of a 2-formylglycine generating enzyme (FGE) to contain a 2-formylglycine (FGly). Such sulfatase motifs may also be referred to herein as an FGE-modification site. Action of FGE is directed in a sequence-specific manner in that the FGE acts at a sulfatase motif positioned within the immunoglobulin polypeptide. The moiety of interest is provided as component of a reactive partner for reaction with an aldehyde of the FGly residue of a converted aldehyde tag of the tagged Ig polypeptide. A wide range of commercially available reagents can be used to accomplish attachment of a moiety of interest to an FGly residue of an aldehyde tagged Ig polypeptide. For example, aminooxy, hydrazide, or thiosemicarbazide derivatives of a number of moieties of interest are suitable reactive partners, and are readily available or can be generated using standard chemical methods.

For example, to attach a poly(ethylene glycol) (PEG) moiety to a tagged Ig polypeptide, an aminooxy-PEG can be generated from monoamino-PEGs and aminooxyglycine using standard protocols. The aminooxy-PEG can then be reacted with a converted (e.g., FGly-modified) aldehyde tagged Ig polypeptide to provide for attachment of the PEG moiety. Delivery of a biotin moiety to a converted aldehyde tagged polypeptide can be accomplished using aminooxy biotin, biotin hydrazide or 2,4 dinitrophenylhydrazine.

A minimal sulfatase motif of an aldehyde tag is usually 5 or 6 amino acid residues in length, usually no more than 6 amino acid residues in length. Sulfatase motifs provided in an Ig polypeptide are at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define a sulfatase motif of less than 16, 15, 14, 13, 12, 11, 10, 9, 8 or 7 amino acid residues in length. In certain embodiments, the sulfatase motif used may be described by the formula:

$$X^1Z^1X^2Z^2X^3Z^3 \qquad (I)$$

where $Z^1$ is cysteine or serine (which can also be represented by (C/S));

$Z^2$ is either a proline or alanine residue (which can also be represented by (P/A));

$Z^3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I;

$X^1$ is present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M, S or V, with the proviso that when the sulfatase motif is at the N-terminus of the target polypeptide, $X^1$ is present; and $X^2$ and $X^3$ independently can be any amino acid, though usually an aliphatic amino acid, a polar, uncharged amino acid, or a sulfur containing amino acid (i.e., other than a aromatic amino acid or a charged amino acid), e.g., S, T, A, V, G or C; e.g., S, T, A, V or G. In one example, the aldehyde tag is of the formula L(C/S)TPSR (SEQ ID NO: 30), e.g., LCTPSR (SEQ ID NO: 31) or LSTPSR (SEQ ID NO: 32). Thus, the present disclosure provides antibodies that include an aldehyde-tagged Ig heavy chain and/or an aldehyde-tagged Ig light chain, where the aldehyde-tagged Ig antibody comprises an Ig constant region amino acid sequence of the heavy and/or light chain contains such a sulfatase motif.

In general, the FGE used to facilitate conversion of cysteine or serine to FGly in a sulfatase motif of an aldehyde tag of a target polypeptide is selected according to the sulfatase motif present in the aldehyde tag. The FGE can be native to the host cell in which the aldehyde tagged polypeptide is expressed, or the host cell can be genetically modified to express an appropriate FGE. In some embodiments it may be desired to use a sulfatase motif compatible with a human FGE, and express the aldehyde tagged protein in a human cell that expresses the FGE or in a host cell, usually a mammalian cell, genetically modified to express a human FGE. In general, an FGE suitable for use in generating an FGly-modified antibody can be obtained from naturally occurring sources or synthetically produced. For example, an appropriate FGE can be derived from biological sources which naturally produce an FGE or which are genetically modified to express a recombinant gene encoding an FGE. Nucleic acids encoding a number of FGEs are known in the art and readily.

Following action of an FGE on the sulfatase motif, $Z_1$ is oxidized to generate a 2-formylglycine (FGly) residue. Furthermore, following both FGE-mediated conversion and reaction with a reactive partner comprising a moiety of interest, FGly position at $Z_1$ in the formula above is covalently bound to the moiety of interest (e.g., detectable label, water soluble polymer, polypeptide, drug, etc.). Thus, the present disclosure provides an anti-CD22 antibody modified to comprise an FGly moiety, wherein the anti-CD22 antibody comprises an FGly-converted sulfatase motif of the formula:

$$X^1(FGly)X^2Z^2X^3Z^3$$

wherein:

$X^1$ is present or absent and, when present, is any amino acid, with the proviso that when the sulfatase motif is at an N-terminus of the polypeptide, $X^1$ is present;

$X^2$ and $X^3$ are each independently any amino acid; and $Z^3$ is a basic amino acid; and where the FGly-modified anti-CD22 antibody presents the FGly group on a solvent-accessible surface when in a folded state. In some embodiments, the FGly-converted sulfatase motif is of the formula L(FGly)TPSR (SEQ ID NO: 33).

As noted above, a subject anti-CD22 antibody modified to include an FGly moiety can be further modified to include a heterologous moiety of interest (e.g., detectable label, water soluble polymer, polypeptide, drug, etc.) covalently bound to the anti-CD22 antibody via the FGly moiety. Thus, the present disclosure provides an anti-CD22 antibody conjugate (also referred to herein as an "anti-CD22 conjugate"), the anti-CD22 conjugate comprising:

$$X^1(FGly')X^2Z^2X^3Z^3 \qquad (I')$$

where

FGly' is the 2-formylglycine residue having a covalently attached moiety;

$Z^2$ is either a proline or alanine residue (which can also be represented by (P/A));

$Z^3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I;

$X^1$ may be present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M or V, with the proviso that when the sulfatase motif is at the N-terminus of the target polypeptide, $X^1$ is present; and $X^2$ and $X^3$ independently can be any amino acid, though usually an aliphatic amino acid, a sulfur-containing amino acid, or a polar, uncharged amino acid, (i.e., other than a aromatic amino acid or a charged amino acid), usually S, T, A, V, G or C, more usually S, T, A, V or G. In some embodiments, the motif is of the formula L(FGly')TPSR (SEQ ID NO: 34).

Drugs

In some cases, an anti-CD22 antibody of the present disclosure comprises drug covalently linked to the heavy and/or light chain of the antibody. "Drugs" include small molecule drugs, peptidic drugs, toxins (e.g., cytotoxins), and the like.

"Small molecule drug" as used herein refers to a compound, e.g., an organic compound, which exhibits a pharmaceutical activity of interest and which is generally of a molecular weight of no greater than about 800 Da, or no greater than 2000 Da, but can encompass molecules of up to 5 kDa and can be as large as about 10 kDa. A small inorganic molecule refers to a molecule containing no carbon atoms, while a small organic molecule refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

In some cases, the drug is a toxin, e.g., a cytotoxin. Ribosome inactivating proteins (RIPs), which are a class of proteins ubiquitous in higher plants, are examples of such cytotoxins. RIPs, which are divided into Type I and Type II classes, are cytotoxic due to their activity as potent inhibitors of eukaryotic protein synthesis. Type I RIPS are composed of a single peptide chain having ribosome-inactivating activity, while Type II proteins are composed of an A-chain, essentially equivalent to a Type I protein, disulfide-linked to a B-chain having cell-binding properties. The N-glycosidic bond of a specific adenine base is hydrolytically cleaved by RIPs in a highly conserved loop region of the 28S rRNA of eukaryotic ribosomes, thereby inactivating translation in eukaryotic cells. See, e.g., U.S. Pat. No. 5,744,580. Gelonin, dodecandrin, tricosanthin, tricokirin, bryodin, Mirabilis antiviral protein (MAP), barley ribosome-inactivating protein (BRIP), pokeweed antiviral proteins (PAPS), saporins, luffins, and momordins are examples of Type I RIPs; whereas ricin and abrin are examples of Type II RIPS. Suitable cytotoxins include, but are not limited to, ricin, abrin, diphtheria toxin, a *Pseudomonas exotoxin* (e.g., PE35, PE37, PE38, PE40, etc.), saporin, gelonin, a pokeweed anti-viral protein (PAP), botulinum toxin, bryodin, momordin, and bouganin.

In some cases, the drug is a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used.

Suitable cancer chemotherapeutic agents include dolastatin and active analogs and derivatives thereof; and auristatin and active analogs and derivatives thereof. See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); and duocarmycins and active analogs and derivatives thereof (e.g., including the synthetic analogues, KW-2189 and CB 1-TM1).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; $17\alpha$-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL□, TAXOTERE□ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202, 448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere□ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Methods of Producing Antibody

A subject antibody can be produced by any known method, e.g., conventional synthetic methods for protein synthesis; recombinant DNA methods; etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med. Chem.* 6:3-10 and Camarero J A et al. 2005 *Protein Pept Lett.* 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983).

Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the polypeptides of the present invention (e.g., polynucleotides encoding immunoglobulins or fragments thereof). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148:1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropane-sulfonic acid (TAPS), etc.; a solubilizing agent; a detergent, e.g., a non-ionic detergent such as Tween-20, etc.; a protease inhibitor; glycerol; and the like.

Nucleic Acids

The present disclosure provides nucleic acids comprising nucleotide sequences encoding a subject antibody. A nucleotide sequence encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP 1 promoter, a GAL7 promoter, a MET25 promoter, a MET3 promoter, a CYC1 promoter, a HIS3 promoter, an ADH1 promoter, a PGK promoter, a GAPDH promoter, an ADC 1 promoter, a TRP 1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) *Proc. Natl. Acad. Sci. U.S.A.* 80:21-25).

A nucleotide sequence encoding a subject antibody can be present in an expression vector and/or a cloning vector. Where a subject antibody comprises two separate polypeptides, nucleotide sequences encoding the two polypeptides can be cloned in the same or separate vectors. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol V is Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol V is Sci 38:2857 2863, 1997; Jomary et al., Gene Ther 4:683 690, 1997, Rolling et al., Hum Gene Ther 10:641648, 1999; Ali et al., Hum Mol Genet 5:591594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, a subject nucleic acid comprises a nucleotide sequence encoding a subject antibody. A subject nucleic acid can comprise a nucleotide sequence encoding anti-CD22 heavy- and light-chains, as described above.

Cells

The present disclosure provides isolated genetically modified host cells (e.g., in vitro cells) that are genetically modified with a subject nucleic acid. In some embodiments, a subject isolated genetically modified host cell can produce a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) 293 cells (ATCC No. CRL1573), HLHepG2 cells, and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

Pharmaceutical Compositions

The present disclosure provides compositions, including pharmaceutical compositions, comprising a subject antibody. In general, a formulation comprises an effective amount of a subject antibody. An "effective amount" means a dosage sufficient to produce a desired result, e.g., reduction in the number of cancerous B cells, reduction in the number and/or activity of autoreactive B cells. In some cases, the desired result is at least a reduction in a symptom of a B cell malignancy, as compared to a control.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM Sucrose; and has a pH of 5.5; or 4) 75 mg/mL of a subject antibody; 0.04% Tween 20 w/v; 20 mM L-histidine; and 250 mM trehalose; and has a pH of 5.5; or 6) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.022% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

Other modes of administration will also find use with the subject invention. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.). Some of these formulations will now be discussed in more detail.

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a B cell malignancy or B cell-mediated autoimmune disorder. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection, e.g., for systemic delivery (e.g., intravenous infusion) or to a local site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Kits with unit doses of a subject antibody, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Treatment Methods

The present disclosure provides methods of treating a disease or disorder associated with or caused by a CD22-positive B cell, e.g., a cancerous CD22-positive B cell; an autoreactive CD22-positive B cell.

Treating B Cell Malignancies

The present disclosure provides methods of treating a B cell malignancy, the methods generally involving administering to an individual in need thereof (e.g., an individual having a B cell malignancy) an effective amount of a subject antibody, alone (e.g., in monotherapy) or in combination (e.g., in combination therapy) with one or more additional therapeutic agents.

B-cell malignancies include, e.g., non-Hodgkin's lymphoma, Burkitt's lymphoma, multiple myeloma, chronic lymphocytic leukemia, hairy cell leukemia and prolymphocytic leukemia.

In some embodiments, an effective amount of a subject antibody is an amount that, when administered alone (e.g., in monotherapy) or in combination (e.g., in combination therapy) with one or more additional therapeutic agents, in one or more doses, is effective to reduce the number of cancerous B cells in an individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the number of cancerous B cells in the individual in the absence of treatment with the antibody.

Combination Therapy

In some embodiments, a subject method of treating a B cell malignancy involves administering a subject antibody and one or more additional therapeutic agents. Suitable additional therapeutic agents include, but are not limited to, a cancer chemotherapeutic agent (as described above).

Treating B Cell-Mediated Autoimmune Disorders

The present disclosure provides methods of treating a B cell-mediated autoimmune disorder, the methods generally involving administering to an individual in need thereof (e.g., an individual having a B cell-mediated autoimmune disorder) an effective amount of a subject antibody, alone (e.g., in monotherapy) or in combination (e.g., in combination therapy) with one or more additional therapeutic agents. B cell-mediated autoimmune disorders are autoimmune disorders in which the pathology is primarily due to the presence of antibody specific for one or more autoantigens. As such, a B cell-mediated autoimmune disorder can also be referred to as an antibody-mediated autoimmune disorder.

B cell-mediated autoimmune disorders include, e.g., systemic lupus erythematosus, myasthenia gravis, autoimmune myocarditis, rheumatoid arthritis, and the like.

In some embodiments, an effective amount of a subject antibody is an amount that, when administered alone (e.g., in monotherapy) or in combination (e.g., in combination therapy) with one or more additional therapeutic agents, in one or more doses, is effective to reduce the number of autoreactive B cells (B cells producing autoantibody) in an individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the number of autoreactive B cells in the individual in the absence of treatment with the antibody.

Combination Therapy

In some embodiments, a subject method of treating a B cell-mediated autoimmune disease involves administering a subject antibody and one or more additional therapeutic agents. Suitable additional therapeutic agents include, but are not limited to, immunosuppressive agents, anti-inflammatory agents, and the like.

Subjects Suitable for Treatment

A variety of subjects are suitable for treatment with a subject method. Suitable subjects include any individual, e.g., a human, who has a B cell malignancy; who has been diagnosed with a B cell malignancy; who has had a B cell malignancy and is at risk for recurrence of the B cell malignancy; who has been treated for a B cell malignancy with an agent other than a subject anti-CD22 antibody (e.g., who has been treated with a cancer chemotherapeutic agent) and who has not responded to the agent; or who has been treated for a B cell malignancy with an agent other than a subject anti-CD22 antibody (e.g., who has been treated with a cancer chemotherapeutic agent) and who initially responded to the agent but subsequently ceased to respond (e.g., relapsed).

Subjects who are suitable for treatment for a B cell-mediated autoimmune disorder using a subject method include any individual e.g., a human, who has a B cell-mediated autoimmune disorder; who has been diagnosed with a B cell-mediated autoimmune disorder; who has had a B cell-mediated autoimmune disorder and is at risk for recurrence of the B cell-mediated autoimmune disorder; who has been treated for a B cell-mediated autoimmune disorder with an agent other than a subject anti-CD22 antibody (e.g., who has been treated with an immunosuppressive agent) and who has not responded to the agent; or who has been treated for a B cell-mediated autoimmune disorder with an agent other than a subject anti-CD22 antibody (e.g., who has been treated with an immunosuppressive agent) and who initially responded to the agent but subsequently ceased to respond (e.g., relapsed).

Detection Methods

The present disclosure provides various detection methods that involve use of a subject antibody. Detection methods include diagnostic methods, prognostic methods, and monitoring methods. A subject detection method generally involves detecting CD22 positive cells, e.g., B cells, e.g., cancerous B cells.

In some embodiments, a subject method is a diagnostic method, e.g., to determine whether an individual has a B cell malignancy.

In some embodiments, a subject method is a monitoring method, e.g., an individual who has been diagnosed as having a B cell malignancy, and is being treated for the disorder, is monitored for response to the treatment and/or progression/regression of the disorder.

In some cases, a subject detection method involves administering to an individual a detectably labeled anti-CD22 antibody of the present disclosure; and detecting binding of the antibody to tissues in the individual. Detection can be achieved, e.g., by magnetic resonance imaging or other suitable imaging technique.

In other instances, a subject detection method involves contacting a detectably labeled anti-CD22 antibody of the present disclosure with a biological sample obtained from an individual; and detecting binding of the antibody to molecules in the biological sample.

The anti-CD22 antibody can be labeled directly or indirectly. Indirect labels include a secondary antibody that comprises a detectable label, where the secondary antibody binds a subject anti-CD22 antibody. Other indirect labels include biotin, where a biotinylated anti-CD22 antibody can be detected using avidin or streptavidin that comprises a detectable label.

Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, $^{125}$I, $^{35}$S, $^{14}$C, or $^{32}$P), enzymes (e.g., horseradish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-dephenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2): 209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

Kits

The present disclosure provides a kit (e.g., a test kit) that includes a subject antibody. A subject kit is useful in carrying out a subject detection method.

A subject kit can include one or more of: a subject antibody, a nucleic acid encoding the same, or a cell comprising a subject nucleic acid. The subject antibody in a subject kit can be humanized. A subject kit can include reagents for labeling the antibody. In some embodiments, the antibody in a subject kit comprises a detectable label.

Other optional components of the kit include: a buffer; a protease inhibitor; a detectable label; etc. Where a subject kit comprises a subject nucleic acid, the nucleic acid may also have restrictions sites, multiple cloning sites, primer sites, etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Commercially available reagents referred to in the Examples were used according to manufacturer's instructions unless otherwise indicated. The source of cells identified in the Examples and throughout the specification by ECACC accession numbers is the European Collection of Cell Cultures (ECACC), Salisbury, England. Unless otherwise defined, all technical and scientific terms used herein have the same meaning as commonly understood by one of ordinary skill in the art to which this invention belongs. Exemplary methods and materials are described below although methods and materials similar or equivalent to those described herein can also be used in the practice or testing of the present invention. The materials, methods, and examples are illustrative only and not intended to be limiting in scope.

Example 1

Generation of Chimeric Antibody

Figure 1B:
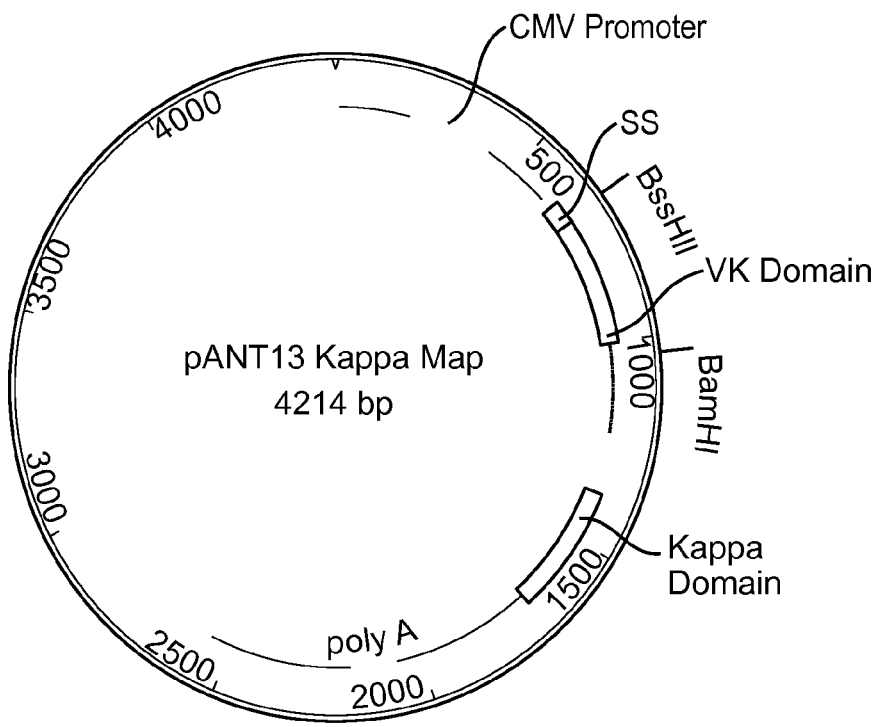
Figure 2A:
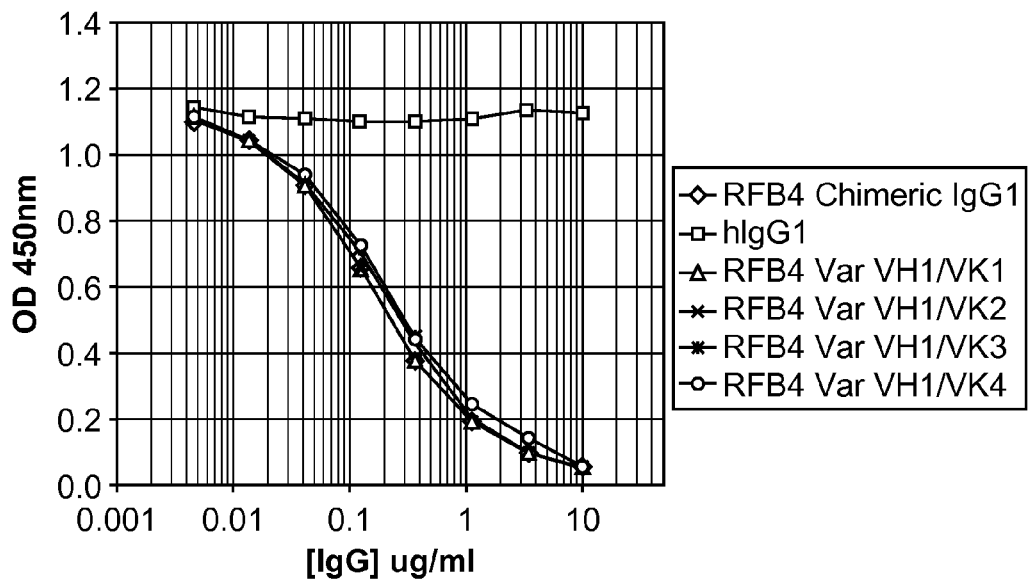
FIGS. 2A-E are graphs depicting competition of humanized anti-CD22 antibodies with biotinylated parental chimeric anti-CD22 antibodies for binding to immobilized CD22.
Figure 2B:
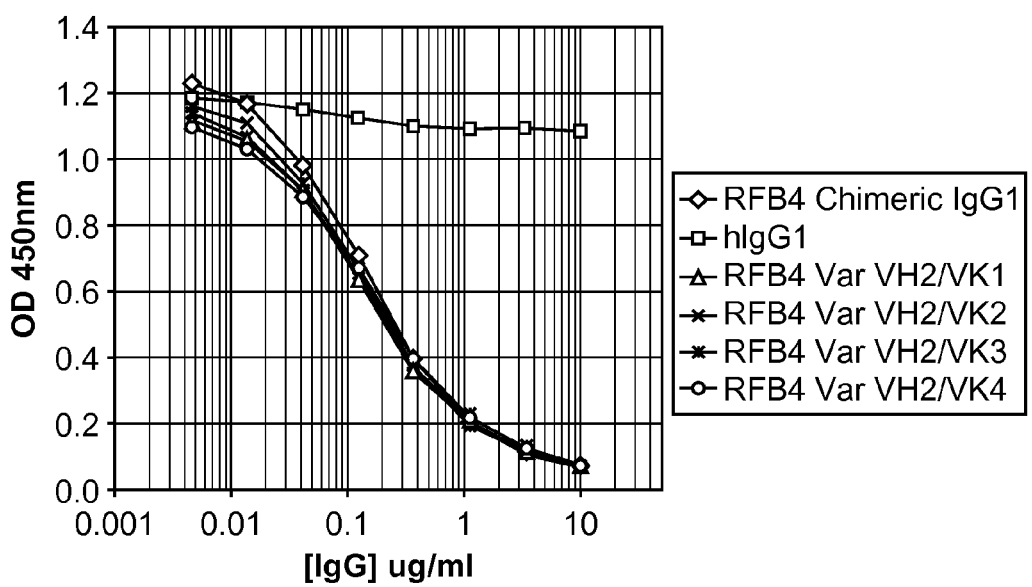
Figure 2C:
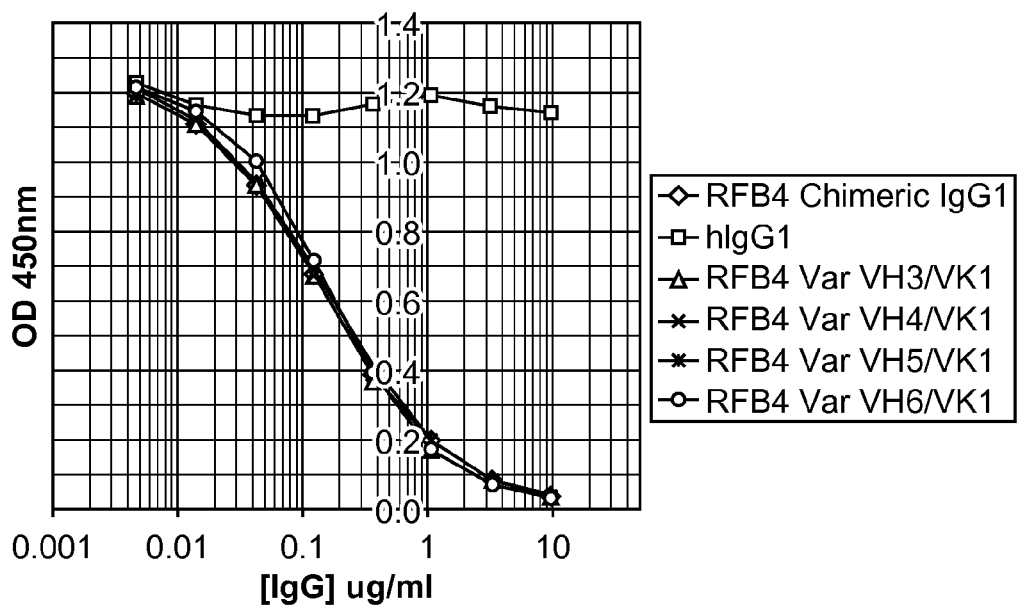
Figure 2D:
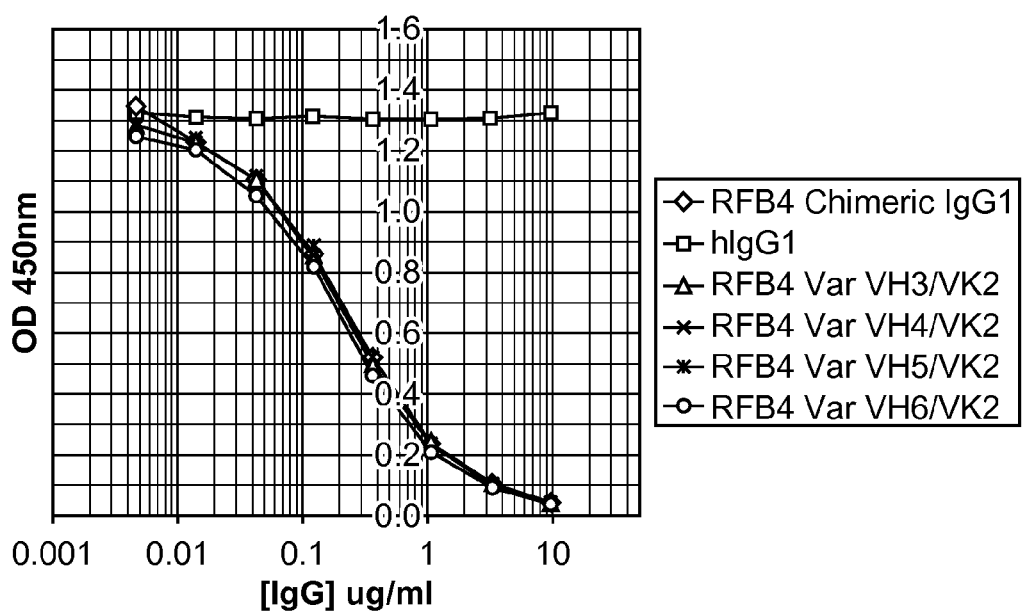
Figure 2E:
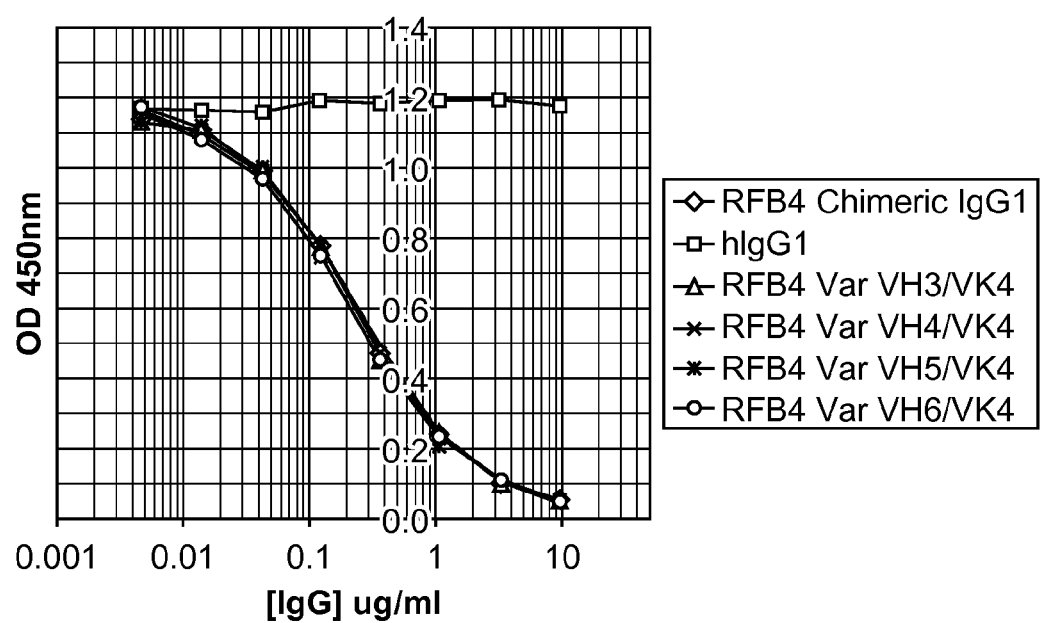

The heavy and light chain variable (V) region sequences of the mouse RFB4 monoclonal antibody (Campana. et al (1985) J. Immunol., 134, 1524-1530. Mansfield et al (1997) Blood. 90, 2020-2026) were synthesized and subcloned into pANT antibody expression vectors (FIG. 1) with heavy and light chain V regions cloned into pANT17 and pANT13 respectively. Heavy chain V region genes were cloned into pANT17 via MluI and HindIII sites in frame with the human γ1 heavy chain gene (G1m3 (G1m(f)) allotype) and light chain V region genes were cloned into pANT13 via BssHII and BamHI sites in frame with the human kappa light chain constant region gene (Km3 allotype). Transcription of both heavy and light chain genes was under the control of the CMV I/E promoter (U.S. Pat. No. 5,168,062 and U.S. Pat. No. 5,385,839, University of Iowa) and the pANT17 plasmid contained a mutant dhfr minigene (Simonsen & Levinson 1983, *Proc. Natl. Acad. Sci. USA* 80:2495-2499) under the control of a SV40 promoter and polyA sequence for selection in eukaryotic cells. Both pANT17 and pANT13 contained a β-lactamase ($Ap^R$) gene for prokaryotic selection and a pMB1 origin of replication for propagation in prokaryotic cells. All plasmids were propagated in *E. coli* DH5 alpha (Invitrogen Cat. No. 18265-017).

The heavy and light chain expression constructs were subsequently co-transfected either transiently into HEK293 c18 cells by calcium phosphate-based transfection or stably transfected into NS0 cells by electroporation. The resulting chimeric RFB4 antibody as secreted from the HEK293 c18 or NS0 cells was purified from the cell culture supernatants by Protein A chromatography and desalted into phosphate-buffered saline (PBS) using PD-10 columns (GE Healthcare Cat. No. 17-0851-01). Concentrations were determined by UV absorbance at 280 nm using a molar extinction coefficient based on the amino acid composition of each individual antibody.

Example 2

Generation of Humanized Antibodies

Humanized antibodies were generated using methods described in EP1844074 (Antitope Ltd). Structural models of the mouse RFB4 V regions were produced using Swiss PDB and analyzed in order to identify important framework amino acids that were likely to be important for the CD22 binding properties of the antibody (constraining residues'). A database of human V region sequences was used to identify segments of human V region sequences containing each of the constraining residues to be used in design of the humanized antibodies. RFB4 CDR sequences were retained in the designed humanized antibody sequences. A set of favored V region sequences were designed and analyzed for the prediction of non-germline major histocompatibility complex (MHC) class II peptide binding by in silico analysis as described in Fothergill et al. (WO9859244, assignee Eclagen Ltd) and also for known $CD4^+$ T-cell epitopes using databases including "The Immune Epitope Database and Analysis Resource", (http://www(dot)immunepitope(dot)org/). V region sequences with predicted non-germline MHC class II binding peptides or with significant hits against T cell epitope databases were discarded. This resulted in a reduced set of V region sequences. Selected heavy and light chain V region sequences were then combined to produce humanized heavy and light chain variable region amino acid sequences. Six heavy chains and four light chain sequences (designated VH1 to VH6, and Vκ1 to Vκ4 respectively) were selected for use in producing humanized RFB4 antibodies. Heavy chains comprising VH sequences VH3 (SEQ ID NO:3), VH4 (SEQ ID NO:4), and VH5 (SEQ ID NO:5), VH6 (SEQ ID NO:6) were paired with light chains comprising VL sequences VK1 (SEQ ID NO:7), VK2 (SEQ ID NO:8), and VK4 (SEQ ID NO:9).

DNA encoding humanized VH and VK variants were synthesized and subcloned into the expression vectors pANT17 and pANT13 (FIG. 1) as described in Example 1. All combinations of humanized VH and Vκ chains were transiently transfected into HEK293 c18 cells and antibody was purified by protein A chromatography from the culture supernatants followed by desalting as described in Example 1.

Example 3

Analysis of Humanised Antibodies

The binding of HEK-derived RFB4 humanized variants to CD22 antigen was assessed in a competition enzyme-linked immunosorbent assay (ELISA) against the parent chimeric antibody. The parental RFB4 chimeric antibody was biotinylated using Biotin Tag™ Micro Biotinylation kit (Sigma-Aldrich). 96 well MaxiSorp plates (Nunc) were coated with 1.0 µg/ml CD22-Fc (R&D Systems Cat. No. 1968SL) in Dulbecco's PBS (PAA Laboratories, Yeovil, UK) (60 µl final volume) at 4° C. overnight. Plates were blocked with Dulbecco's PBS-2% BSA for 1 hour at room temperature. Plates were washed 3 times with wash buffer (0.05% Tween20 in Dulbecco's-PBS). Test humanized antibodies at various concentrations were premixed with biotinylated parent chimeric antibody (0.04 µg/ml final concentration) and then added to the CD22-Fc plate (60 µl final volume). All samples were tested in duplicate. Plates were incubated for 1 h at room temperature and washed 3 times with wash buffer. 60 µl of a 1 in 1000 dilution of Streptavidin horse radish peroxidase (HRP) (Sigma-Aldrich) was added and incubated for 1 hour at room temperature. Plates were washed 3 times with wash buffer and 60 µl of 3,3',5,5'-tetramethybenzidine (TMB) substrate (Invitrogen) was added and incubated at room temperature in the dark to allow the colour to develop. The reaction was stopped by adding 50 µl of 3M HCl. Plates were read at 450 nm using Dynex plate reader.

As shown in FIG. 2, all lead humanized RFB4 variants displayed competitive binding profiles similar to the parent chimeric antibody. The $IC_{50}$ of chimeric RFB4 and humanized RFB4 antibodies, relative to wild-type RFB4 IgG1 antibody, is shown in Table 2, below.

TABLE 2

| Construct | $IC_{50}$ relative to Chimeric RFB4 IgG1 |
|---|---|
| Chimeric RFB4 | 1.0 |
| VH3/VK1 | 0.8 |
| VH3/VK2 | 1.0 |
| VH3/VK4 | 1.1 |
| VH4/VK1 | 0.9 |
| VH4/VK2 | 1.1 |
| VH4/VK4 | 1.0 |
| VH5/VK1 | 0.9 |
| VH5/VK2 | 1.0 |
| VH5/VK4 | 1.0 |
| VH6/VK1 | 0.9 |
| VH6/VK2 | 1.0 |
| VH6/VK4 | 1.0 |

Example 4

Analysis of CD4+ T Cell Responses

Peripheral blood mononuclear cells (PBMC) were isolated from healthy community donor buffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee. PBMC were isolated from buffy coats by Lymphoprep (Axis-shield, Dundee, UK) density centrifugation and $CD8^+$ T cells were depleted using $CD8^+$ RosetteSep™ (StemCell Technologies Inc, London, UK). Donors were characterized by identifying HLA-DR haplotypes using an HLA single-specific-primer polymerase chain reaction (SSP-PCR) based tissue-typing kit (Biotest, Solihull, UK). T cell responses to a 'reproducibility' control antigen (Keyhole Limpet Haemocyanin (KLH), Pierce (Perbio), Cramlington, UK) as well as control peptides derived from Influenza A and Epstein Barr viruses were also determined. PBMC were then frozen and stored in liquid nitrogen until required.

The chimeric and lead VH4/VK1, VH5/VK1, VH6/VK4 humanized antibodies were purified from transiently transfected HEK293 c18 cell lines by Protein A chromatography followed by size exclusion chromatography using a 26/60 Superdex 5200 column (GE Healthcare) in 1×PBS. Monomeric peak fractions were collected, quantified and endotoxin levels analyzed for all preparations using the Endosafe®-PTS™ (Charles River, Margate, UK) system.

A cohort of 20 donors was selected to best represent the number and frequency of HLA-DR allotypes expressed in the world population. Analysis of the allotypes expressed in the cohort against those expressed in the world population revealed that all major HLA-DR alleles (individual allotypes with a frequency >5% expressed in the world population) were well represented. PBMCs from each donor were revived in AIM-V® culture medium (Invitrogen, Paisley, UK), washed and resuspended in AIM-V® to $4-6 \times 10^6$ PBMC/ml. For each donor, bulk cultures were established in which 1 ml proliferation cell stock was added to the appropriate wells of a 24 well plate. 0.5 ml culture medium together with 0.5 ml of each diluted test sample were added to the PBMC to give a final concentration of 50 μg/ml per sample. For each donor, a reproducibility control (cells incubated with 100 μg/ml KLH) and a culture medium only well were also included. Cultures were incubated for a total of 8 days at 37° C. with 5% $CO_2$. On days 5, 6, 7 and 8, the cells in each well were gently resuspended and 3×100 μl aliquots transferred to each well of a round bottomed 96 well plate. The cultures were pulsed with 0.75 μCi [$^3$H]-Thymidine (Perkin Elmer®, Beaconsfield, UK) in 100 μl AIM-V® culture medium and incubated for a further 18 hours before harvesting onto filter mats (Perkin Elmer®) using a TomTec Mach III cell harvester. Counts per minute (cpm) for each well were determined by Meltilex™ (Perkin Elmer®) scintillation counting on a 1450 Microbeta Wallac Trilux Liquid Scintillation Counter (Perkin Elmer®) in paralux, low background counting.

For proliferation assays, an empirical threshold of a Stimulation Index (SI) equal to or greater than 2 (SI≥2.0) has been previously established whereby samples inducing proliferative responses above this threshold are deemed positive (where included, borderline SIs≥1.90 are highlighted). For proliferation data sets (n=3), positive responses were defined by statistical and empirical thresholds:
  1) Significance (p<0.05) of the response by comparing cpm of test wells against medium control wells using unpaired two sample student's t-test.
  2) SI equal to or greater than 2 (SI≥2.0).
  3) Basal cpm>150 cpm In addition, intra-assay variation was assessed by calculating the CVs and SDs of the raw data from replicate cultures.

FIGS. 3A-D depict healthy donor T cell proliferation responses to test antibodies. PBMC from bulk cultures were sampled and assessed for proliferation on days 5, 6, 7, and 8 after incubation with the three test samples. Proliferation responses with an SI≥2.0 (p<0.05), indicated by the dotted line that were significant (p<0.05) using an unpaired, two sample Student's t test were considered positive.

Figure 3A:
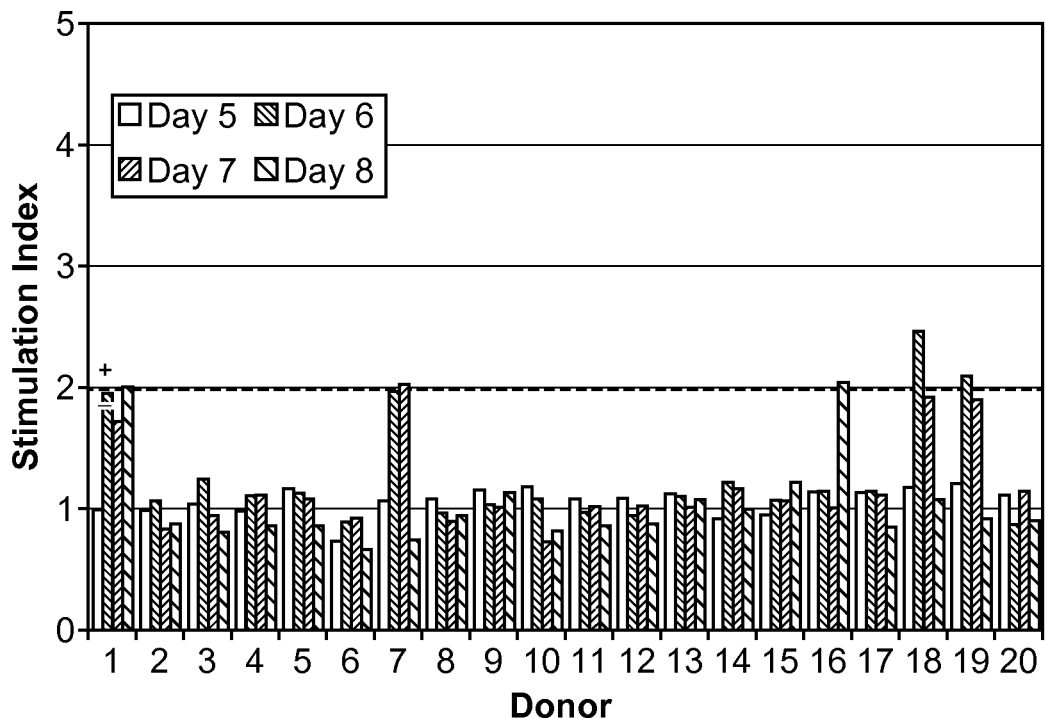
FIGS. 3A-D depict healthy donor T cell proliferation responses to test antibodies.
Figure 3B:
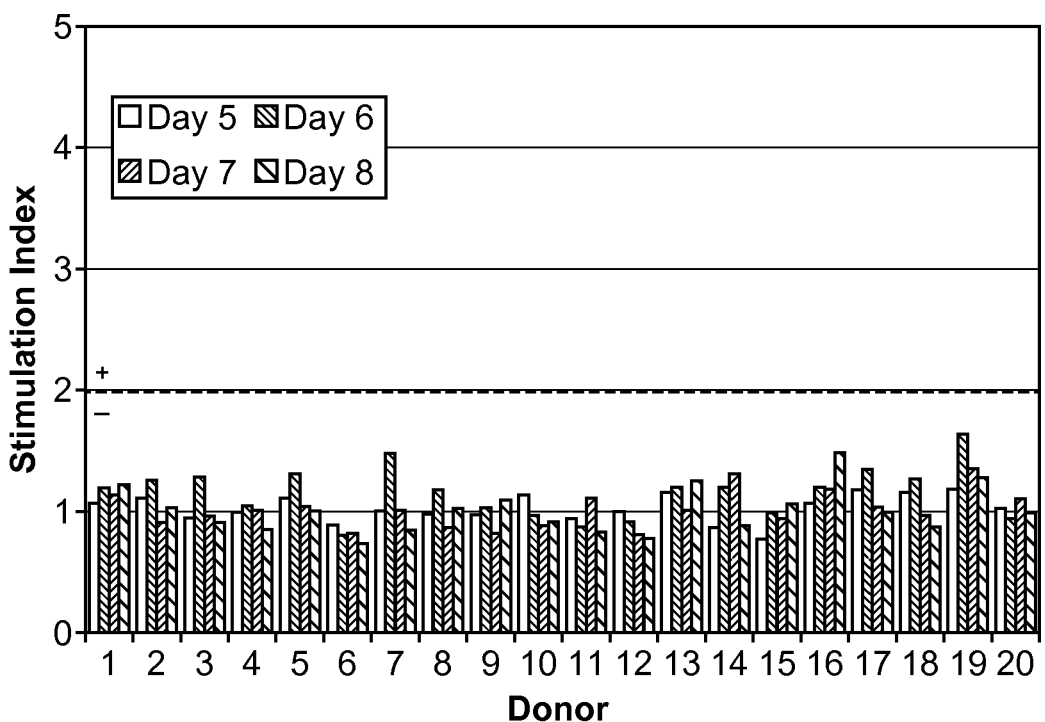
Figure 3C:
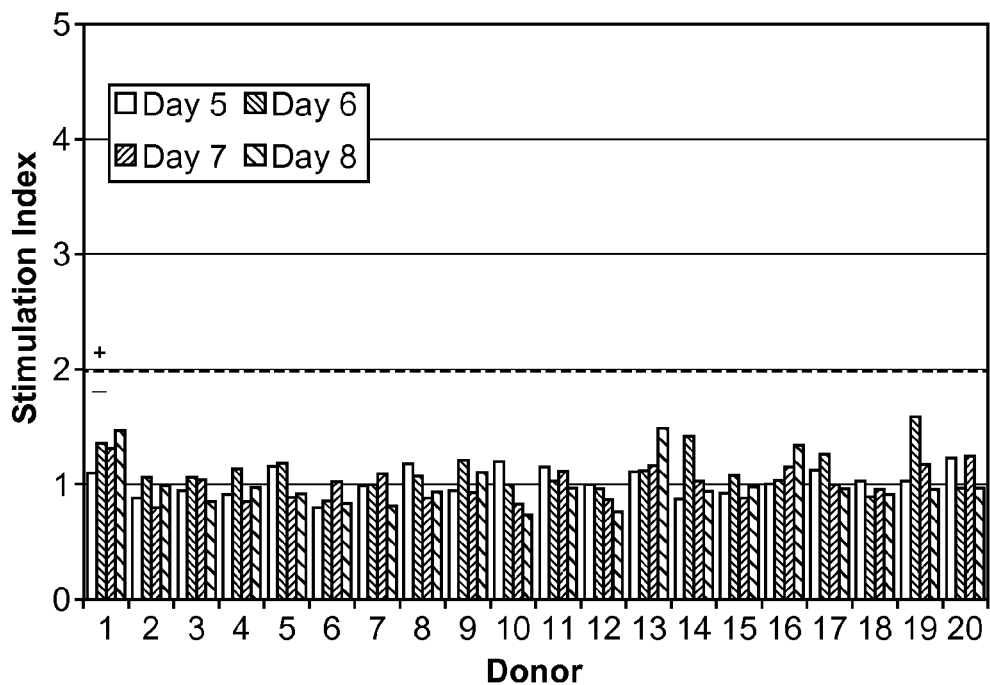
Figure 3D:
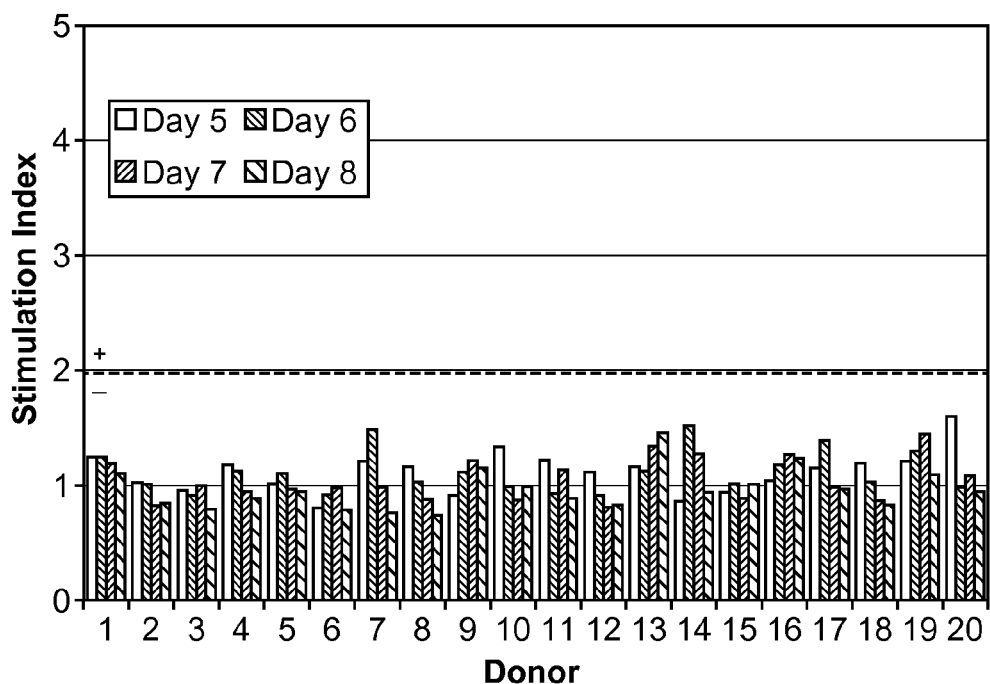

The data are shown in FIGS. 3A-D, and are summarized in Table 3, below. FIGS. 3A-D illustrate the donor SI responses to each of the test antibodies throughout the time course. The fully humanised anti-CD22 antibodies (VH4/VK1, VH5/VK1, VH6/VK4) induced no positive responses using SI≥2.0, p<0.05 threshold in any of the donors in the proliferation assay, whereas the chimeric anti-CD22 antibody induced positive T cell proliferation responses in 25% of donors. FIG. 3A: chimeric antibody; FIG. 3B: VH4/VK1; FIG. 3C: VH5/VK1; FIG. 3D: VH6/VK4.

TABLE 3

Summary of healthy donor proliferation.

| | Anti-CD22 | | | | |
|---|---|---|---|---|---|
| | Chimeric | VH4/VK1 | VH5/VK1 | VH6/VK4 | KLH |
| Donor 1 | P | | | | |
| Donor 2 | | | | | |
| Donor 3 | | | | | P* |
| Donor 4 | | | | | |
| Donor 5 | | | | | |
| Donor 6 | | | | | |
| Donor 7 | P | | | | P |
| Donor 8 | | | | | P |
| Donor 9 | | | | | P |
| Donor 10 | | | | | |
| Donor 11 | | | | | P |
| Donor 12 | | | | | P |
| Donor 13 | | | | | P |
| Donor 14 | | | | | P |
| Donor 15 | | | | | P |
| Donor 16 | P | | | | P |

TABLE 3-continued

Summary of healthy donor proliferation.

| | Anti-CD22 | | | |
|---|---|---|---|---|
| | Chimeric | VH4/VK1 | VH5/VK1 | VH6/VK4 | KLH |
| Donor 17 | | | | | P |
| Donor 18 | P | | | | P |
| Donor 19 | P | | | | P |
| Donor 20 | | | | | P |
| Proliferation % | 25 | 0 | 0 | 0 | 70 |

Positive proliferation ("P") responses from days 5-8 (SI ≥ 2.0, significant p < 0.05) throughout the time course (SI ≥ 2.0, significant p < 0.05). Borderline responses (significant p < 0.05 with SI ≥ 1.90) for proliferation (P*) are shown. The total frequency of response in the donor cohort is shown as a percentage.

Example 5

Analysis of Internalization

Raji cells, grown to ~0.5×10$^6$ cells/mL, were used at 0.35-0.5×10$^6$ cells per test. Cells were resuspended at 100 μL/tube in phosphate buffered saline+1% fetal calf serum (FCS; Buffer A). Controls included cells exposed only to 4° C. or to both 4° and 37° C. that were incubated with no antibody or with secondary antibody only. Primary antibody was added at 1 μg/tube and cells were incubated on ice for 30 min. Then, cells were washed: 1 mL Buffer A was added, cells were gently pelleted by centrifugation, and supernatant was removed. This was repeated for a total of 2 washes. Cells to be exposed to 37° C. were resuspended in 37° C. RMPI+10% fetal calf serum (FCS), 2 mM glutamine, and incubated at 37° C., 5% CO$_2$ for 45 min. Next, cells were washed one time in 1 mL ice-cold Buffer A. Secondary antibody (fluorescein-conjugated goat anti-human Fc; Jackson Immunoresearch, West Grove, Pa.) was added at a 1:100 dilution in Buffer A and cells were incubated on ice for 30 min. Finally, cells were washed twice in ice-cold Buffer A and resuspended in 300 μL Buffer A. Cells were kept in the dark at 4° C. and analyzed within 18 h by flow cytometry on a Becton Dickinson FACSCanto using FACSDiva software.

Figure 4:
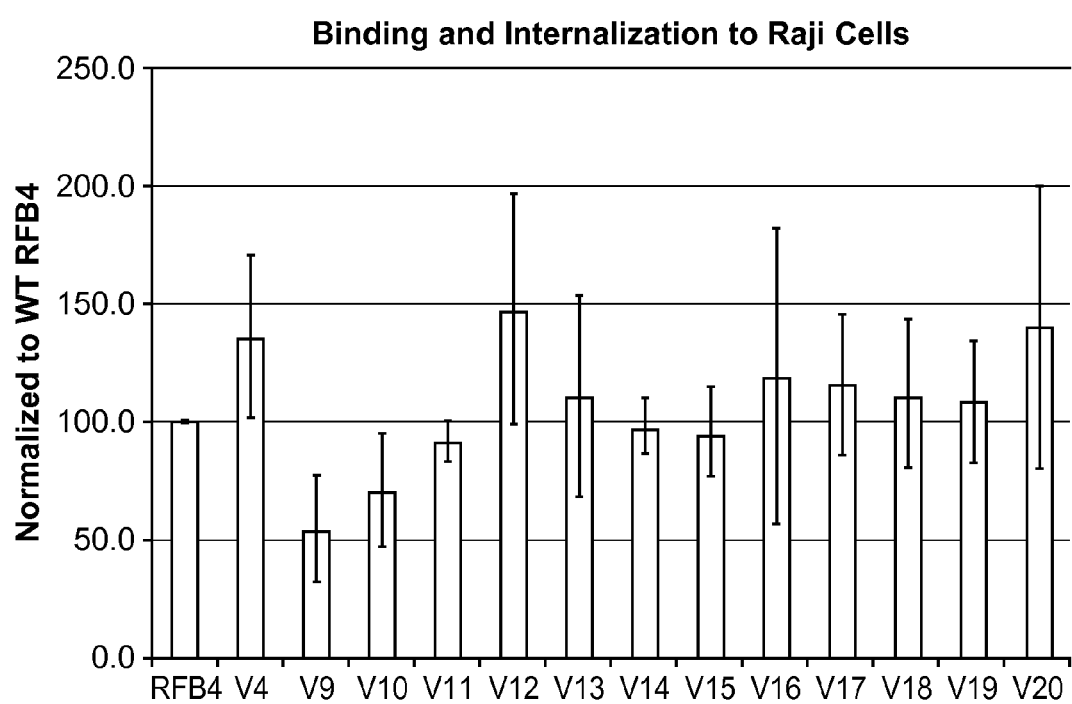
FIG. 4 depicts binding of humanized anti-CD22 antibodies to Raji cells, and internalization of the antibodies by the Raji cells.
Figure 6A:
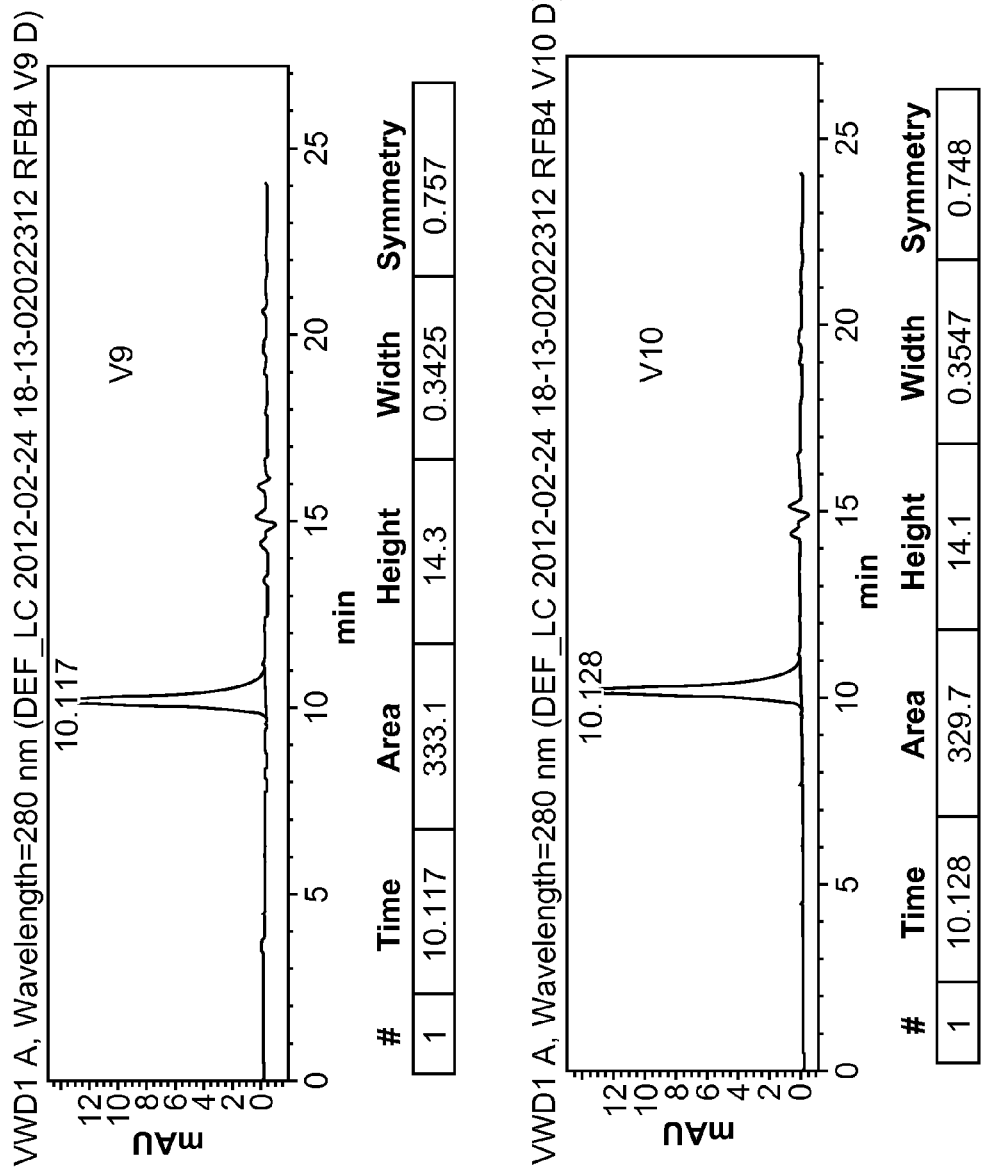
FIGS. 6A-6D depict aggregation of humanized anti-CD22 variants.
Figure 6B:
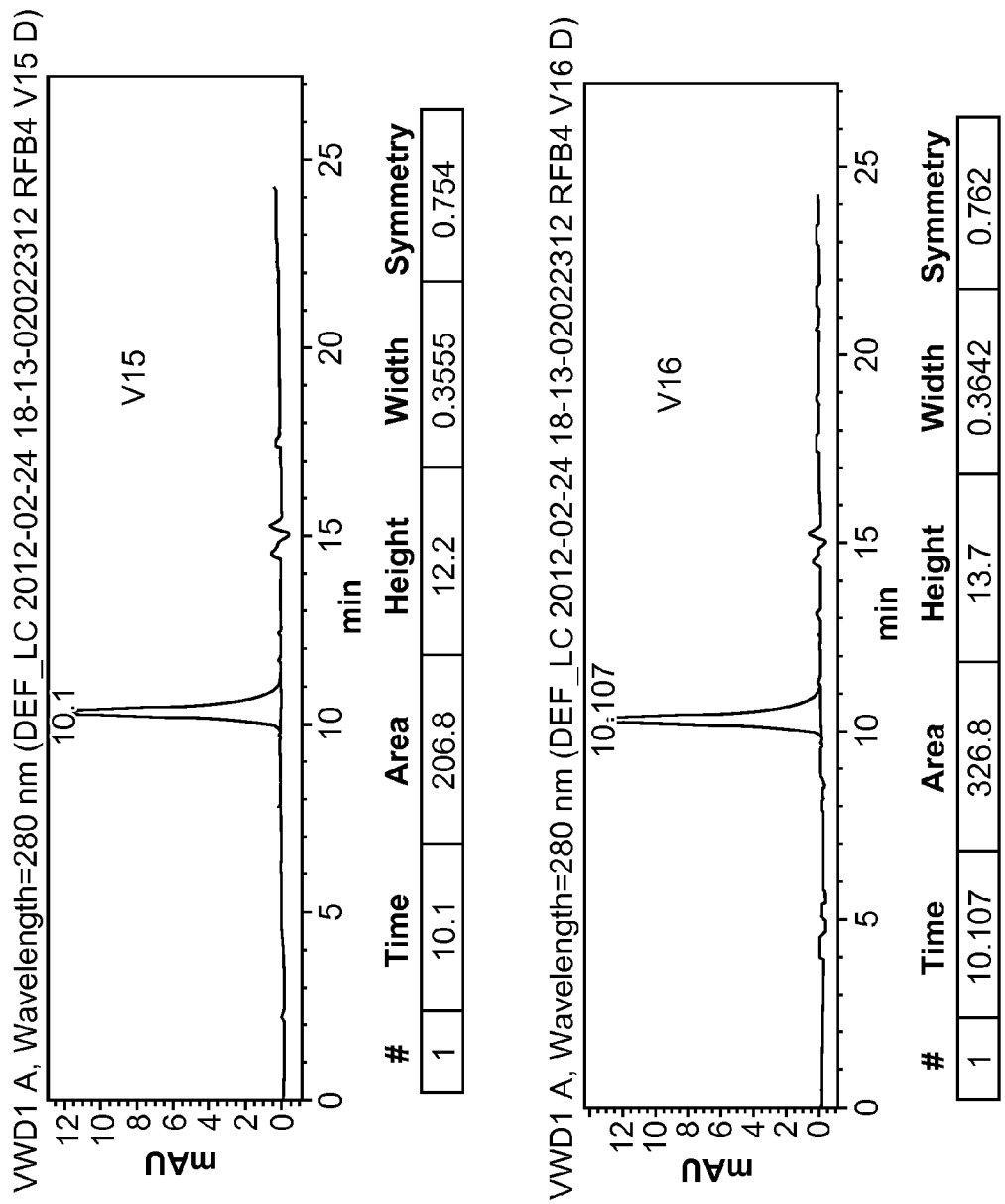
Figure 6C:
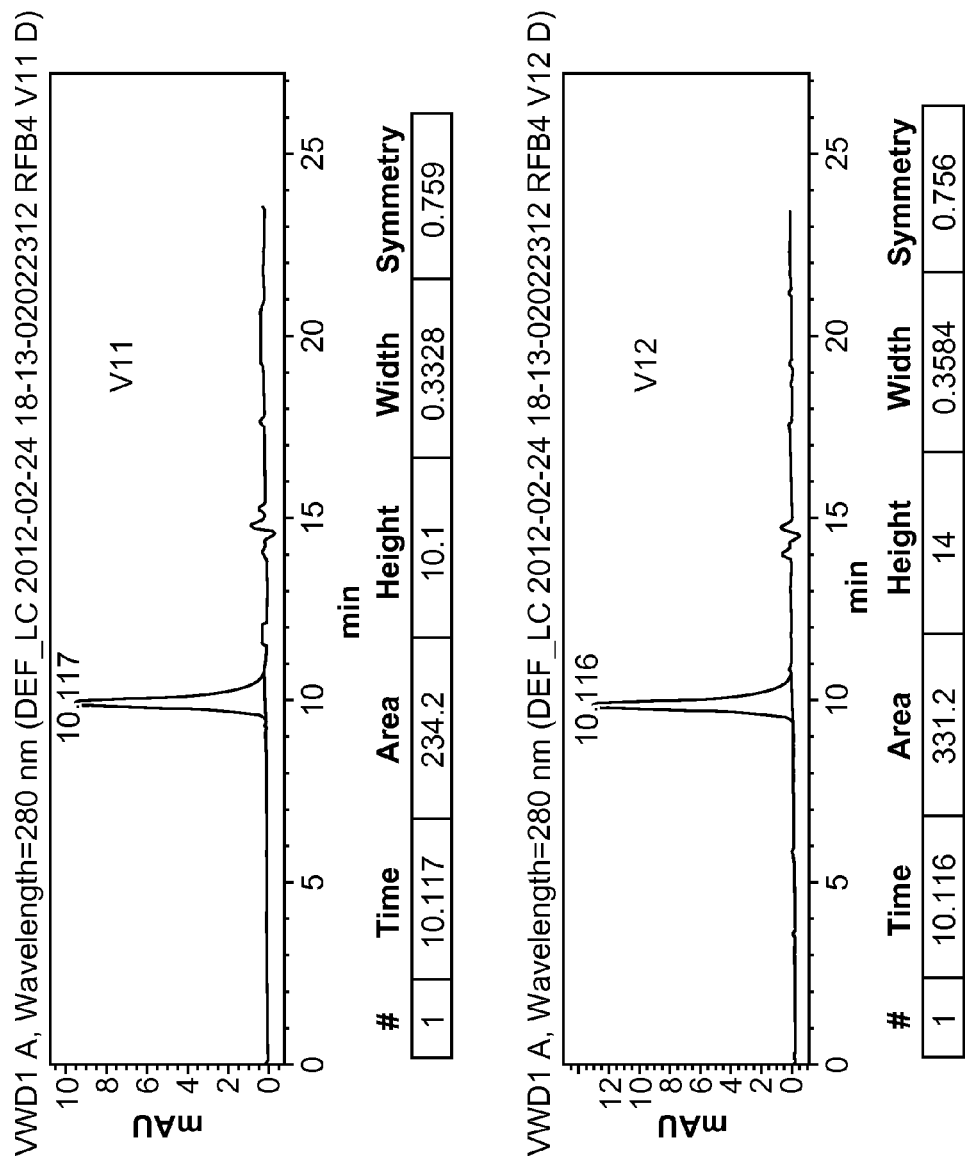
Figure 6D:
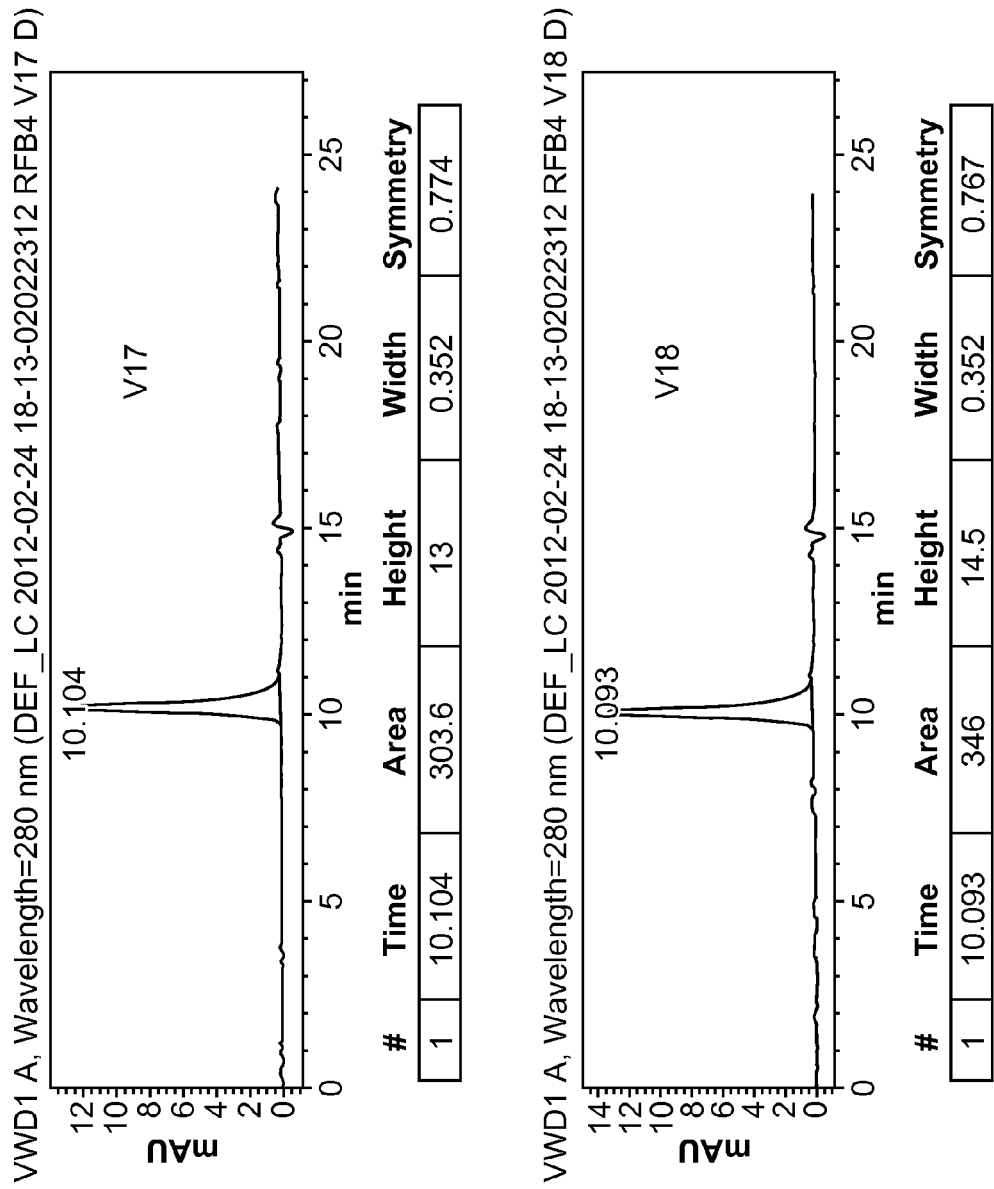

Data were analyzed as follows: the mean fluorescence intensity (MFI) of the secondary antibody on the FL1 channel (used to detect fluorescein) was subtracted from the MFI of the signals generated when primary antibodies were included. The resulting values were then termed the MFI signals for the current experiment. The MFI values of cells held at 4° C. represented the binding of the antibody to the cell surface. The MFI values of cells exposed to 37° C. represented the signal generated by antibody remaining at the cell surface after internalization of CD22-Ab complexes. The difference between the MFI at 4° and 37° C. corresponds to the internalization of bound antibody (FIG. 4). To allow for comparison among experiments performed on different days, binding and internalization values were sometimes normalized to the wild-type antibody, RFB4.

Example 6

Analysis of CD22 Binding Affinity

Human CD22 was obtained from either from R&D Systems (huCD22-Fc form, catalog #1968-SL-050) or from Sino Biological Inc (huCD22 with His tag, catalog #11958-H08H) and was biotinylated to Lys using a LC-biotin. The binding of variants 12 through 20 to huCD22 was measured using a ForteBio instrument. StreptAvidin derivatized ForteBio biosensors were loaded with the biotinylated huCD22 molecules. The concentrations of the antibodies of interest were confirmed by $A_{280}$ and loaded biosensors were exposed to increasing concentrations of each of the antibodies. The kinetic association and dissociation rates were determined toward the huCD22 at 4-5 concentrations at pH 7.25 and the $K_D$'s were determined (FIG. 5).

Example 7

Analysis of Aggregation

To determine the extent of aggregation of the RFB4 variants, 20 μg of antibody was analyzed using size-exclusion high-performance liquid chromatography (Tosoh #08541 G300 SW$_{XL}$ 7.8 mm×30 cm; mobile phase 25 mM sodium phosphate buffer, 300 mM NaCl, pH 6.8; 0.8 mL/min; monitor absorbance at 220 nm and 280 nm). Results are highlighted in FIGS. 6A-6D.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. An antibody that specifically binds an epitope in CD22, wherein the antibody comprises:
   a) an immunoglobulin heavy chain comprising a VH region having the amino acid sequence EVQLVESGGGLV KPGGSLX$_1$LSCAASGFAFSIYDMSWVRQAPGKG LEWVAYISSGGGTTYYPDTVKGRFTISRDNAKN X$_2$ LYLQMX$_3$SLRAEDTAMYYCARHSGYGSSYG VLFAYWGQGTLVTVSS (SEQ ID NO:1), where X$_1$ is K or R; X$_2$ is S or T; and X$_3$ is N or S; and
   b) an immunoglobulin light chain.

2. The antibody of claim 1, wherein the immunoglobulin light chain comprises the amino acid sequence DIQMTQSPSSLSASVGDRVTIT-CRASQDISNYLNWYQQK-PGKAVKLLIYYTSILHSGVPSRFSGS GSGTDYTLTISS-LQQEDFATYFCQQGNTLPWTFGGGTKVEIK (SEQ ID NO:7; VK1).

3. The antibody of claim 1, wherein the immunoglobulin light chain comprises the amino acid sequence DIQMTQSPSSLSASVGDRVTIT-CRASQDISNYLNWYQQK-PGKAVKLLIYYTSILHSGVPSRFSGS GSGTDYTLTISS-LQPEDFATYFCQQGNTLPWTFGGGTKVEIK (SEQ ID NO:8; VK2).

4. The antibody of claim 1, wherein the immunoglobulin light chain comprises the amino acid sequence DIQMTQSPSSVSASVGDRVTIT-CRASQDISNYLNWYQQKPGKAP-KLLIYYTSILHSGVPSRFSGS GSGTDYTLTISSLQPED-FATYFCQQGNTLPWTFGGGTKVEIK (SEQ ID NO:9; VK4).

5. An antibody that specifically binds an epitope in CD22, wherein the antibody comprises:
   a) an immunoglobulin light chain comprising the amino acid sequence DIQMTQSPSSX$_1$SASVGDRVTITCR ASQDISNYLNWYQQKPGKAX$_2$KLLIYYTSILHSG VPSRFSG SGSGTDYTLTISSLQX$_3$EDFATYFCQQG NTLPWTFGGGTKVEIK (SEQ ID NO:2), where X$_1$ is L (Leu) or V (Val); X$_2$ is V or P; and X$_3$ is Q or P; and
   b) an immunoglobulin heavy chain.

6. The antibody of claim 5, wherein the immunoglobulin heavy chain comprises an amino acid sequence selected from:
   EVQLVESGGGLVKPGGSLKLSCAASG-FAFSIYDMSWVRQAPGKGLEWVAYISSGGGTT YYPDTVKGRFTISRDNAKNTLYLQMSSL-RAEDTAMYYCARHSGYGSSYGVLFAYWGQ GTLVTVSS (SEQ ID NO:3; VH3);
   EVQLVESGGGLVKPGGSLRLSCAASG-FAFSIYDMSWVRQAPGKGLEWVAYISSGGGTT YYPDTVKGRFTISRDNAKNSLYLQMSSL-RAEDTAMYYCARHSGYGSSYGVLFAYWGQ GTLVTVSS (SEQ ID NO:4; VH4);
   EVQLVESGGGLVKPGGSLKLSCAASG-FAFSIYDMSWVRQAPGKGLEWVAYISSGGGTT YYPDTVKGRFTISRDNAKNSLYLQMNSL-RAEDTAMYYCARHSGYGSSYGVLFAYWGQ GTLVTVSS (SEQ ID NO:5; VH5); and
   EVQLVESGGGLVKPGGSLKLSCAASG-FAFSIYDMSWVRQAPGKGLEWVAYISSGGGTT YYPDTVKGRFTISRDNAKNSLYLQMSSL-RAEDTAMYYCARHSGYGSSYGVLFAY-WGQGTLVT VSS (SEQ ID NO:6; VH6).

7. The antibody of claim 1, wherein the light chain region and the heavy chain region are present in separate polypeptides.

8. The antibody of claim 1, wherein the light chain region and the heavy chain region are present in a single polypeptide.

9. The antibody of claim 1, wherein the antibody binds the epitope with an affinity of from about $10^7$ M$^{-1}$ to about $10^{12}$ M$^{-1}$.

10. The antibody of claim 1, wherein the heavy chain region is of the isotype IgG1, IgG2, IgG3, or IgG4.

11. The antibody of claim 1, wherein the antibody is detectably labeled.

12. The antibody of claim 1, wherein the antibody is a Fv, scFv, Fab, F(ab')2, or Fab'.

13. The antibody of claim 1, wherein the antibody comprises a covalently linked non-peptide synthetic polymer.

14. The antibody of claim 1, wherein the synthetic polymer is poly(ethylene glycol) polymer.

15. The antibody of claim 1, wherein the antibody comprises a covalently linked lipid or fatty acid moiety.

16. The antibody of claim 1, wherein the antibody comprises a covalently linked polysaccharide or carbohydrate moiety.

17. The antibody of claim 1, wherein the antibody comprises a contrast agent.

18. The antibody of claim 1, wherein the antibody comprises an affinity domain.

19. The antibody of claim 1, wherein the antibody is immobilized on a solid support.

20. The antibody of claim 1, wherein the antibody is a single chain Fv (scFv) antibody.

21. The antibody of claim 20, wherein the scFv is multimerized.

22. The antibody of claim 1, wherein the antibody comprises a covalently linked cytotoxin.

23. The antibody of claim 1, wherein the antibody comprises a constant region amino acid sequence comprising an amino acid sequence of a sulfatase motif.

24. The antibody of claim 1, wherein the antibody comprises a constant region amino acid sequence comprising an amino acid sequence of a sulfatase motif, and wherein the sulfatase motif is modified to comprise a 2-formylglycine (FGly) moiety.

25. The antibody of claim 24, wherein the antibody comprises a heterologous moiety covalently linked to the antibody via the FGly moiety.

26. The antibody of claim 25, wherein the heterologous moiety is selected from a drug, a toxin, a detectable label, a water-soluble polymer, and a synthetic peptide.

27. A recombinant expression vector comprising a nucleotide sequence encoding the antibody of claim 1, wherein the nucleotide sequence is operably linked to a transcriptional control element that is active in a eukaryotic cell.

28. A pharmaceutical composition comprising:
   a) the antibody of claim 1; and
   b) a pharmaceutically acceptable carrier.

29. The pharmaceutical composition of claim 28, wherein the antibody is encapsulated in a liposome.

30. A method of treating B cell malignancy in a subject, the method comprising:
   administering to a subject having cancer an effective amount of the pharmaceutical composition of claim 28.

* * * * *

UNITED STATES PATENT AND TRADEMARK OFFICE
CERTIFICATE OF CORRECTION

PATENT NO. : 9,181,343 B2  
APPLICATION NO. : 13/942140  
DATED : November 10, 2015  
INVENTOR(S) : David Rabuka et al.

Page 1 of 1

It is certified that error appears in the above-identified patent and that said Letters Patent is hereby corrected as shown below:

IN THE CLAIMS

In column 76, line 27, "(FG1y)" should read -- (FGly) --.

In column 76, line 30, "the FG1y moiety" should read -- the FGly moiety --.

Signed and Sealed this  
Twenty-third Day of February, 2016

Michelle K. Lee  
*Director of the United States Patent and Trademark Office*

SEQUENCE LISTING

```
<160> NUMBER OF SEQ ID NOS: 38

<210> SEQ ID NO 1
<211> LENGTH: 123
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
```

-continued

```
<222> LOCATION: (84)..(84)
<223> OTHER INFORMATION: Xaa can be any naturally occurring amino acid

<400> SEQUENCE: 1

Glu Val Gln Leu Val Glu Ser Gly Gly Gly Leu Val Lys Pro Gly Gly
1               5                   10                  15

Ser Leu Xaa Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Xaa Leu Tyr
65                  70                  75                  80

Leu Gln Met Xaa Ser Leu Arg Ala Glu Asp Thr Ala Met Tyr Tyr Cys
            85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120

<210> SEQ ID NO 2
<211> LENGTH: 107
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid

<400> SEQUENCE: 2

Asp Ile Gln Met Thr Gln Ser Pro Ser Ser Xaa Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Lys Pro Gly Lys Ala Xaa Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Leu Thr Ile Ser Ser Leu Gln Xaa
65                  70                  75                  80

Glu Asp Phe Ala Thr Tyr Phe Cys Gln Gln Gly Asn Thr Leu Pro Trp
            85                  90                  95

Thr Phe Gly Gly Gly Thr Lys Val Glu Ile Lys
            100                 105

<210> SEQ ID NO 3
<211> LENGTH: 123
<212> TYPE: PRT
<213> ORGANISM: Artificial sequence
<220> FEATURE:
<223> OTHER INFORMATION: Synthetic amino acid sequence
```

<400> SEQUENCE: 3

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
            115                 120
```

<210> SEQ ID NO 4
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 4

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
            115                 120
```

<210> SEQ ID NO 5
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 5

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Ala Pro Gly Lys Gly Leu Glu Trp Val
        35                  40                  45
```

```
Ala Tyr Ile Ser Ser Gly Gly Gly Thr Thr Tyr Tyr Pro Asp Thr Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Met Tyr Tyr Cys
                 85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
            115                 120

<210> SEQ ID NO 6
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 6

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Ala Phe Ser Ile Tyr
             20                  25                  30

Asp Met Ser Trp Val Arg Gln Ala Pro Gly Lys Gly Leu Glu Trp Val
         35                  40                  45

Ala Tyr Ile Ser Ser Gly Gly Gly Thr Thr Tyr Tyr Pro Asp Thr Val
     50                  55                  60

Lys Gly Arg Phe Thr Ile Ser Arg Asp Asn Ala Lys Asn Ser Leu Tyr
 65                  70                  75                  80

Leu Gln Met Ser Ser Leu Arg Ala Glu Asp Thr Ala Met Tyr Tyr Cys
                 85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
            115                 120

<210> SEQ ID NO 7
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Val Lys Leu Leu Ile
         35                  40                  45

Tyr Tyr Thr Ser Ile Leu His Ser Gly Val Pro Ser Arg Phe Ser Gly
     50                  55                  60

Ser Gly Ser Gly Thr Asp Tyr Thr Leu Thr Ile Ser Ser Leu Gln Gln
 65                  70                  75                  80

Glu Asp Phe Ala Thr Tyr Phe Cys Gln Gln Gly Asn Thr Leu Pro Trp
                 85                  90                  95

Thr Phe Gly Gly Gly Thr Lys Val Glu Ile Lys
```

100 105

<210> SEQ ID NO 8
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Val Glu Ile Lys
            100                 105

<210> SEQ ID NO 9
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 9

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Val Glu Ile Lys
            100                 105

<210> SEQ ID NO 10
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 10

Cys Tyr Pro Tyr Asp Val Pro Asp Tyr Ala
1               5                   10

<210> SEQ ID NO 11

```
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 11

Asp Tyr Lys Asp Asp Asp Asp Lys
1               5

<210> SEQ ID NO 12
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 12

Cys Glu Gln Lys Leu Ile Ser Glu Glu Asp Leu
1               5                   10

<210> SEQ ID NO 13
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 13

His His His His His
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 14

His His His His His His
1               5

<210> SEQ ID NO 15
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 15

Glu Gln Lys Leu Ile Ser Glu Glu Asp Leu
1               5                   10

<210> SEQ ID NO 16
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 16

Asp Tyr Lys Asp Asp Asp Asp Lys
1               5

<210> SEQ ID NO 17
<211> LENGTH: 8
```

```
<212> TYPE: PRT
<213> ORGANISM: Artificial sequence
<220> FEATURE:
<223> OTHER INFORMATION: Synthetic amino acid sequence

<400> SEQUENCE: 17

Trp Ser His Pro Gln Phe Glu Lys
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 18

Tyr Pro Tyr Asp Val Pro Asp Tyr Ala
1               5

<210> SEQ ID NO 19
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 19

Arg Tyr Ile Arg Ser
1               5

<210> SEQ ID NO 20
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 20

Phe His His Thr
1

<210> SEQ ID NO 21
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 21

Trp Glu Ala Ala Ala Arg Glu Ala Cys Cys Arg Glu Cys Cys Ala Arg
1               5                   10                  15

Ala

<210> SEQ ID NO 22
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 22

Gly Ser Gly Gly Ser
1               5

<210> SEQ ID NO 23
```

```
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 23

Gly Gly Gly Ser
1

<210> SEQ ID NO 24
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 24

Gly Gly Ser Gly
1

<210> SEQ ID NO 25
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 25

Gly Gly Ser Gly Gly
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 26

Gly Ser Gly Ser Gly
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 27

Gly Ser Gly Gly Gly
1               5

<210> SEQ ID NO 28
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 28

Gly Gly Gly Ser Gly
1               5

<210> SEQ ID NO 29
<211> LENGTH: 5
```

```
<212> TYPE: PRT
<213> ORGANISM: Artificial sequence
<220> FEATURE:
<223> OTHER INFORMATION: Synthetic amino acid sequence

<400> SEQUENCE: 29

Gly Ser Ser Ser Gly
1               5

<210> SEQ ID NO 30
<211> LENGTH: 6
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: Xaa is C or S.

<400> SEQUENCE: 30

Leu Xaa Thr Pro Ser Arg
1               5

<210> SEQ ID NO 31
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 31

Leu Cys Thr Pro Ser Arg
1               5

<210> SEQ ID NO 32
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 32

Leu Ser Thr Pro Ser Arg
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: MOD_RES
<222> LOCATION: (2)..(2)
<223> OTHER INFORMATION: The G at this position is a 2 formylglycine.

<400> SEQUENCE: 33

Leu Gly Thr Pro Ser Arg
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: MOD_RES
```

```
<222> LOCATION: (2)..(2)
<223> OTHER INFORMATION: The G at this position is a 2 formylglycine
      residue having a covalently attached moiety.

<400> SEQUENCE: 34

Leu Gly Thr Pro Ser Arg
1               5

<210> SEQ ID NO 35
<211> LENGTH: 759
<212> TYPE: PRT
<213> ORGANISM: Homo sapiens

<400> SEQUENCE: 35

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
        50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Pro Pro Lys Lys Val Thr Thr
                325                 330                 335
```

```
Val Ile Gln Asn Pro Met Pro Ile Arg Glu Gly Asp Thr Val Thr Leu
            340                 345                 350

Ser Cys Asn Tyr Asn Ser Ser Asn Pro Ser Val Thr Arg Tyr Glu Trp
            355                 360                 365

Lys Pro His Gly Ala Trp Glu Glu Pro Ser Leu Gly Val Leu Lys Ile
        370                 375                 380

Gln Asn Val Gly Trp Asp Asn Thr Thr Ile Ala Cys Ala Ala Cys Asn
385                 390                 395                 400

Ser Trp Cys Ser Trp Ala Ser Pro Val Ala Leu Asn Val Gln Tyr Ala
                405                 410                 415

Pro Arg Asp Val Arg Val Arg Lys Ile Lys Pro Leu Ser Glu Ile His
                420                 425                 430

Ser Gly Asn Ser Val Ser Leu Gln Cys Asp Phe Ser Ser His Pro
            435                 440                 445

Lys Glu Val Gln Phe Phe Trp Glu Lys Asn Gly Arg Leu Leu Gly Lys
        450                 455                 460

Glu Ser Gln Leu Asn Phe Asp Ser Ile Ser Pro Glu Asp Ala Gly Ser
465                 470                 475                 480

Tyr Ser Cys Trp Val Asn Asn Ser Ile Gly Gln Thr Ala Ser Lys Ala
                485                 490                 495

Trp Thr Leu Glu Val Leu Tyr Ala Pro Arg Arg Leu Arg Val Ser Met
            500                 505                 510

Ser Pro Gly Asp Gln Val Met Glu Gly Lys Ser Ala Thr Leu Thr Cys
        515                 520                 525

Glu Ser Asp Ala Asn Pro Pro Val Ser His Tyr Thr Trp Phe Asp Trp
        530                 535                 540

Asn Asn Gln Ser Leu Pro Tyr His Ser Gln Lys Leu Arg Leu Glu Pro
545                 550                 555                 560

Val Lys Val Gln His Ser Gly Ala Tyr Trp Cys Gln Gly Thr Asn Ser
                565                 570                 575

Val Gly Lys Gly Arg Ser Pro Leu Ser Thr Leu Thr Val Tyr Tyr Ser
            580                 585                 590

Pro Glu Thr Ile Gly Arg Arg Val Ala Val Gly Leu Gly Ser Cys Leu
        595                 600                 605

Ala Ile Leu Ile Leu Ala Ile Cys Gly Leu Lys Leu Gln Arg Arg Trp
        610                 615                 620

Lys Arg Thr Gln Ser Gln Gln Gly Leu Gln Glu Asn Ser Ser Gly Gln
625                 630                 635                 640

Ser Phe Phe Val Arg Asn Lys Lys Val Arg Arg Ala Pro Leu Ser Glu
                645                 650                 655

Gly Pro His Ser Leu Gly Cys Tyr Asn Pro Met Met Glu Asp Gly Ile
            660                 665                 670

Ser Tyr Thr Thr Leu Arg Phe Pro Glu Met Asn Ile Pro Arg Thr Gly
        675                 680                 685

Asp Ala Glu Ser Ser Glu Met Gln Arg Pro Pro Asp Cys Asp Asp
        690                 695                 700

Thr Val Thr Tyr Ser Ala Leu His Lys Arg Gln Val Gly Asp Tyr Glu
705                 710                 715                 720

Asn Val Ile Pro Asp Phe Pro Glu Asp Glu Gly Ile His Tyr Ser Glu
                725                 730                 735

Leu Ile Gln Phe Gly Val Gly Glu Arg Pro Gln Ala Gln Glu Asn Val
            740                 745                 750
```

```
Asp Tyr Val Ile Leu Lys His
            755
```

<210> SEQ ID NO 36
<211> LENGTH: 670
<212> TYPE: PRT
<213> ORGANISM: Homo sapiens

<400> SEQUENCE: 36

```
Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
        50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
                100                 105                 110

Asp Ser Gly Gln Leu Gly Leu Arg Met Glu Ser Lys Thr Glu Lys Trp
            115                 120                 125

Met Glu Arg Ile His Leu Asn Val Ser Glu Arg Pro Phe Pro Pro His
        130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Pro Pro Lys Lys Val Thr Thr Val Ile Gln Asn Pro Met Pro Ile Arg
                245                 250                 255

Glu Gly Asp Thr Val Thr Leu Ser Cys Asn Tyr Asn Ser Ser Asn Pro
            260                 265                 270

Ser Val Thr Arg Tyr Glu Trp Lys Pro His Gly Ala Trp Glu Glu Pro
        275                 280                 285

Ser Leu Gly Val Leu Lys Ile Gln Asn Val Gly Trp Asp Asn Thr Thr
    290                 295                 300

Ile Ala Cys Ala Ala Cys Asn Ser Trp Cys Ser Trp Ala Ser Pro Val
305                 310                 315                 320

Ala Leu Asn Val Gln Tyr Ala Pro Arg Asp Val Arg Val Arg Lys Ile
                325                 330                 335

Lys Pro Leu Ser Glu Ile His Ser Gly Asn Ser Val Ser Leu Gln Cys
            340                 345                 350

Asp Phe Ser Ser Ser His Pro Lys Glu Val Gln Phe Phe Trp Glu Lys
        355                 360                 365
```

```
Asn Gly Arg Leu Leu Gly Lys Glu Ser Gln Leu Asn Phe Asp Ser Ile
            370                 375                 380

Ser Pro Glu Asp Ala Gly Ser Tyr Ser Cys Trp Val Asn Asn Ser Ile
385                 390                 395                 400

Gly Gln Thr Ala Ser Lys Ala Trp Thr Leu Glu Val Leu Tyr Ala Pro
                405                 410                 415

Arg Arg Leu Arg Val Ser Met Ser Pro Gly Asp Gln Val Met Glu Gly
            420                 425                 430

Lys Ser Ala Thr Leu Thr Cys Glu Ser Asp Ala Asn Pro Pro Val Ser
                435                 440                 445

His Tyr Thr Trp Phe Asp Trp Asn Asn Gln Ser Leu Pro Tyr His Ser
            450                 455                 460

Gln Lys Leu Arg Leu Glu Pro Val Lys Val Gln His Ser Gly Ala Tyr
465                 470                 475                 480

Trp Cys Gln Gly Thr Asn Ser Val Gly Lys Gly Arg Ser Pro Leu Ser
                485                 490                 495

Thr Leu Thr Val Tyr Tyr Ser Pro Glu Thr Ile Gly Arg Arg Val Ala
            500                 505                 510

Val Gly Leu Gly Ser Cys Leu Ala Ile Leu Ile Leu Ala Ile Cys Gly
                515                 520                 525

Leu Lys Leu Gln Arg Arg Trp Lys Arg Thr Gln Ser Gln Gln Gly Leu
530                 535                 540

Gln Glu Asn Ser Ser Gly Gln Ser Phe Phe Val Arg Asn Lys Lys Val
545                 550                 555                 560

Arg Arg Ala Pro Leu Ser Glu Gly Pro His Ser Leu Gly Cys Tyr Asn
                565                 570                 575

Pro Met Met Glu Asp Gly Ile Ser Tyr Thr Thr Leu Arg Phe Pro Glu
            580                 585                 590

Met Asn Ile Pro Arg Thr Gly Asp Ala Glu Ser Ser Glu Met Gln Arg
            595                 600                 605

Pro Pro Pro Asp Cys Asp Asp Thr Val Thr Tyr Ser Ala Leu His Lys
610                 615                 620

Arg Gln Val Gly Asp Tyr Glu Asn Val Ile Pro Asp Phe Pro Glu Asp
625                 630                 635                 640

Glu Gly Ile His Tyr Ser Glu Leu Ile Gln Phe Gly Val Gly Glu Arg
                645                 650                 655

Pro Gln Ala Gln Glu Asn Val Asp Tyr Val Ile Leu Lys His
            660                 665                 670

<210> SEQ ID NO 37
<211> LENGTH: 846
<212> TYPE: PRT
<213> ORGANISM: Homo sapiens

<400> SEQUENCE: 37

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
50                  55                  60

Asn Lys Asn Thr Ser Lys Phe Asp Gly Thr Arg Leu Tyr Glu Ser Thr
```

```
                65                  70                  75                  80
Lys Asp Gly Lys Val Pro Ser Glu Gln Lys Arg Val Gln Phe Leu Gly
                    85                  90                  95

Asp Lys Asn Lys Asn Cys Thr Leu Ser Ile His Pro Val His Leu Asn
                    100                 105                 110

Asp Ser Gly Gln Leu Gly Leu Arg Met Glu Ser Lys Thr Glu Lys Trp
                    115                 120                 125

Met Glu Arg Ile His Leu Asn Val Ser Glu Arg Pro Phe Pro Pro His
                130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                    165                 170                 175

Leu Leu Glu Gly Val Pro Met Arg Gln Ala Ala Val Thr Ser Thr Ser
                180                 185                 190

Leu Thr Ile Lys Ser Val Phe Thr Arg Ser Glu Leu Lys Phe Ser Pro
                    195                 200                 205

Gln Trp Ser His His Gly Lys Ile Val Thr Cys Gln Leu Gln Asp Ala
                210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                    245                 250                 255

Glu Gly Asp Ser Val Thr Met Thr Cys Glu Val Ser Ser Ser Asn Pro
                260                 265                 270

Glu Tyr Thr Thr Val Ser Trp Leu Lys Asp Gly Thr Ser Leu Lys Lys
                    275                 280                 285

Gln Asn Thr Phe Thr Leu Asn Leu Arg Glu Val Thr Lys Asp Gln Ser
                290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                    325                 330                 335

Gln Ile Leu His Ser Pro Ala Val Glu Gly Ser Gln Val Glu Phe Leu
                340                 345                 350

Cys Met Ser Leu Ala Asn Pro Leu Pro Thr Asn Tyr Thr Trp Tyr His
                    355                 360                 365

Asn Gly Lys Glu Met Gln Gly Arg Thr Glu Glu Lys Val His Ile Pro
                370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                    405                 410                 415

Tyr Pro Pro Lys Lys Val Thr Thr Val Ile Gln Asn Pro Met Pro Ile
                420                 425                 430

Arg Glu Gly Asp Thr Val Thr Leu Ser Cys Asn Tyr Asn Ser Ser Asn
                435                 440                 445

Pro Ser Val Thr Arg Tyr Glu Trp Lys Pro His Gly Ala Trp Glu Glu
                    450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                    485                 490                 495
```

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
            515                 520                 525

Cys Asp Phe Ser Ser Ser His Pro Lys Glu Val Gln Phe Phe Trp Glu
        530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
            565                 570                 575

Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
            595                 600                 605

Gly Lys Ser Ala Thr Leu Thr Cys Glu Ser Asp Ala Asn Pro Pro Val
            610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
            645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
            675                 680                 685

Ala Val Gly Leu Gly Ser Cys Leu Ala Ile Leu Ile Leu Ala Ile Cys
            690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
            725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
            755                 760                 765

Glu Met Asn Ile Pro Arg Thr Gly Asp Ala Glu Ser Ser Glu Met Gln
            770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
            805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys
            835                 840                 845

<210> SEQ ID NO 38
<211> LENGTH: 751
<212> TYPE: PRT
<213> ORGANISM: Homo sapiens

<400> SEQUENCE: 38

Met His Leu Leu Gly Pro Trp Leu Leu Leu Leu Val Leu Glu Tyr Leu
1               5                   10                  15

Ala Phe Ser Asp Ser Ser Lys Trp Val Phe Glu His Pro Glu Thr Leu

-continued

```
                   20                  25                  30
Tyr Ala Trp Glu Gly Ala Cys Val Trp Ile Pro Cys Thr Tyr Arg Ala
                35                  40                  45
Leu Asp Gly Asp Leu Glu Ser Phe Ile Leu Phe His Asn Pro Glu Tyr
 50                  55                  60
Asn Lys Asn Thr Ser Lys Phe Asp Gly Thr Arg Leu Tyr Glu Ser Thr
 65                  70                  75                  80
Lys Asp Gly Lys Val Pro Ser Glu Gln Lys Arg Val Gln Phe Leu Gly
                85                  90                  95
Asp Lys Asn Lys Asn Cys Thr Leu Ser Ile His Pro Val His Leu Asn
                100                 105                 110
Asp Ser Gly Gln Leu Gly Leu Arg Met Glu Ser Lys Thr Glu Lys Trp
                115                 120                 125
Met Glu Arg Ile His Leu Asn Val Ser Glu Arg Pro Phe Pro Pro His
                130                 135                 140
Ile Gln Leu Pro Pro Glu Ile Gln Glu Ser Gln Glu Val Thr Leu Thr
145                 150                 155                 160
Cys Leu Leu Asn Phe Ser Cys Tyr Gly Tyr Pro Ile Gln Leu Gln Trp
                165                 170                 175
Leu Leu Glu Gly Val Pro Met Arg Gln Ala Ala Val Thr Ser Thr Ser
                180                 185                 190
Leu Thr Ile Lys Ser Val Phe Thr Arg Ser Glu Leu Lys Phe Ser Pro
                195                 200                 205
Gln Trp Ser His His Gly Lys Ile Val Thr Cys Gln Leu Gln Asp Ala
                210                 215                 220
Asp Gly Lys Phe Leu Ser Asn Asp Thr Val Gln Leu Asn Val Lys His
225                 230                 235                 240
Thr Pro Lys Leu Glu Ile Lys Val Thr Pro Ser Asp Ala Ile Val Arg
                245                 250                 255
Glu Gly Asp Ser Val Thr Met Thr Cys Glu Val Ser Ser Ser Asn Pro
                260                 265                 270
Glu Tyr Thr Thr Val Ser Trp Leu Lys Asp Gly Thr Ser Leu Lys Lys
                275                 280                 285
Gln Asn Thr Phe Thr Leu Asn Leu Arg Glu Val Thr Lys Asp Gln Ser
                290                 295                 300
Gly Lys Tyr Cys Cys Gln Val Ser Asn Asp Val Gly Pro Gly Arg Ser
305                 310                 315                 320
Glu Glu Val Phe Leu Gln Val Gln Tyr Ala Pro Glu Pro Ser Thr Val
                325                 330                 335
Gln Ile Leu His Ser Pro Ala Val Glu Gly Ser Gln Val Glu Phe Leu
                340                 345                 350
Cys Met Ser Leu Ala Asn Pro Leu Pro Thr Asn Tyr Thr Trp Tyr His
                355                 360                 365
Asn Gly Lys Glu Met Gln Gly Arg Thr Glu Glu Lys Val His Ile Pro
                370                 375                 380
Lys Ile Leu Pro Trp His Ala Gly Thr Tyr Ser Cys Val Ala Glu Asn
385                 390                 395                 400
Ile Leu Gly Thr Gly Gln Arg Gly Pro Gly Ala Glu Leu Asp Val Gln
                405                 410                 415
Tyr Pro Pro Lys Lys Val Thr Thr Val Ile Gln Asn Pro Met Pro Ile
                420                 425                 430
Arg Glu Gly Asp Thr Val Thr Leu Ser Cys Asn Tyr Asn Ser Ser Asn
                435                 440                 445
```

```
Pro Ser Val Thr Arg Tyr Glu Trp Lys Pro His Gly Ala Trp Glu Glu
    450                 455             460
Pro Ser Leu Gly Val Leu Lys Ile Gln Asn Val Gly Trp Asp Asn Thr
465             470                 475             480
Thr Ile Ala Cys Ala Ala Cys Asn Ser Trp Cys Ser Trp Ala Ser Pro
                485             490             495
Val Ala Leu Asn Val Gln Tyr Ala Pro Arg Asp Val Arg Val Arg Lys
            500             505             510
Ile Lys Pro Leu Ser Glu Ile His Ser Gly Asn Ser Val Ser Leu Gln
        515             520             525
Cys Asp Phe Ser Ser Ser His Pro Lys Glu Val Gln Phe Phe Trp Glu
    530             535             540
Lys Asn Gly Arg Leu Leu Gly Lys Glu Ser Gln Leu Asn Phe Asp Ser
545             550             555             560
Ile Ser Pro Glu Asp Ala Gly Ser Tyr Ser Cys Trp Val Asn Asn Ser
            565             570             575
Ile Gly Gln Thr Ala Ser Lys Ala Trp Thr Leu Glu Val Leu Tyr Ala
        580             585             590
Pro Arg Arg Leu Arg Val Ser Met Ser Pro Gly Asp Gln Val Met Glu
    595             600             605
Gly Lys Ser Ala Thr Leu Thr Cys Glu Ser Asp Ala Asn Pro Pro Val
610             615             620
Ser His Tyr Thr Trp Phe Asp Trp Asn Asn Gln Ser Leu Pro Tyr His
625             630             635             640
Ser Gln Lys Leu Arg Leu Glu Pro Val Lys Val Gln His Ser Gly Ala
            645             650             655
Tyr Trp Cys Gln Gly Thr Asn Ser Val Gly Lys Gly Arg Ser Pro Leu
        660             665             670
Ser Thr Leu Thr Val Tyr Tyr Ser Pro Glu Thr Ile Gly Arg Arg Val
    675             680             685
Ala Val Gly Leu Gly Ser Cys Leu Ala Ile Leu Ile Leu Ala Ile Cys
    690             695             700
Gly Leu Lys Leu Gln Arg Arg Trp Lys Arg Thr Gln Ser Gln Gln Gly
705             710             715             720
Leu Gln Glu Asn Ser Ser Gly Gln Ser Phe Phe Val Arg Asn Lys Lys
            725             730             735
Arg Cys Arg Val Leu Arg Asp Ala Glu Thr Ser Pro Gly Leu Arg
            740             745             750
```